US011266840B2

(12) United States Patent
Chae

(10) Patent No.: US 11,266,840 B2
(45) Date of Patent: Mar. 8, 2022

(54) WIRELESS CARDIAC PACE MAKING

(71) Applicant: Arizona Board of Regents on behalf of Arizona State University, Scottsdale, AZ (US)

(72) Inventor: Junseok Chae, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/453,581

(22) Filed: Jun. 26, 2019

(65) Prior Publication Data

US 2020/0001089 A1 Jan. 2, 2020

Related U.S. Application Data

(60) Provisional application No. 62/690,789, filed on Jun. 27, 2018.

(51) Int. Cl.
*A61N 1/368* (2006.01)
*A61N 1/378* (2006.01)
(Continued)

(52) U.S. Cl.
CPC ............ *A61N 1/3684* (2013.01); *A61B 5/318* (2021.01); *A61N 1/3682* (2013.01); *A61N 1/3787* (2013.01); *A61N 1/37223* (2013.01)

(58) Field of Classification Search
CPC .... A61N 1/3684; A61B 5/0428; A61B 5/0402
See application file for complete search history.

(56) References Cited

U.S. PATENT DOCUMENTS 4,041,954 A * 8/1977 Ohara .................. A61N 1/3787
600/510
6,790,178 B1 9/2004 Mault et al.
(Continued)

FOREIGN PATENT DOCUMENTS

WO 2009064577 A1 5/2009
WO 2010088219 A2 8/2010
(Continued)

OTHER PUBLICATIONS

Sweeney, Michael O., A New Paradigm for Physiologic Ventricular Pacing, Journal of the American College of Cardiology, p. 282-288, Jan. 17, 2006.
(Continued)

*Primary Examiner* — Brian T Gedeon
*Assistant Examiner* — Joshua Andrew Schum-Houck
(74) *Attorney, Agent, or Firm* — Troutman Pepper Hamilton Sanders LLP

(57) ABSTRACT

Systems, devices, and methods involving cardiac pace making are provided. Implantable wireless pace making systems, devices, and methods using electromagnetic waveforms to interact with subcutaneous implanted sensors or stimulators, or both, are described. Systems, devices, and methods can include wireless, miniaturized, battery-free, radiofrequency (RF) microwave activated, sensors or stimulators or integrated sensor/stimulators that are implanted in multiple thoracic cavity locations, and interact with a remote pace making control-module or multiple modules.

15 Claims, 8 Drawing Sheets

(51) Int. Cl.
    A61N 1/372    (2006.01)
    A61B 5/318    (2021.01)

(56) References Cited

U.S. PATENT DOCUMENTS

| | | | |
|---|---|---|---|
| 6,871,084 B1* | 3/2005 | Kingsley | A61B 5/30 600/372 |
| 6,889,086 B2 | 5/2005 | Mass et al. | |
| 8,019,419 B1 | 9/2011 | Panescu et al. | |
| 8,129,622 B2 | 3/2012 | Taylor et al. | |
| 8,321,021 B2* | 11/2012 | Kisker | A61N 1/3787 607/32 |
| 8,345,910 B2 | 1/2013 | Chae et al. | |
| 8,725,270 B2 | 5/2014 | Towe | |
| 8,909,343 B2 | 12/2014 | Towe | |
| 8,923,963 B2 | 12/2014 | Bonner et al. | |
| 9,168,383 B2 | 10/2015 | Jacobson et al. | |
| 9,358,136 B2 | 6/2016 | Stein et al. | |
| 9,409,029 B2 | 8/2016 | Perryman et al. | |
| 9,446,255 B2 | 11/2016 | Towe et al. | |
| 9,623,253 B2 | 4/2017 | Perryman et al. | |
| 9,693,708 B2 | 7/2017 | Towe | |
| 9,700,712 B2 | 7/2017 | Towe | |
| 9,935,498 B2 | 4/2018 | Joshi | |
| 10,119,960 B2 | 11/2018 | Chae et al. | |
| 10,576,305 B2 | 3/2020 | Maharbiz et al. | |
| 11,000,257 B2 | 5/2021 | Adler et al. | |
| 2006/0020224 A1 | 1/2006 | Geiger | |
| 2006/0235484 A1 | 10/2006 | Jaax et al. | |
| 2008/0183247 A1* | 7/2008 | Harding | A61N 1/3684 607/60 |
| 2008/0275356 A1 | 11/2008 | Stasz et al. | |
| 2009/0204170 A1* | 8/2009 | Hastings | A61N 1/3756 607/33 |
| 2009/0299216 A1 | 12/2009 | Chen et al. | |
| 2010/0016762 A1 | 1/2010 | Thapliyal et al. | |
| 2010/0198039 A1* | 8/2010 | Towe | A61B 5/076 600/373 |
| 2010/0324378 A1 | 12/2010 | Tran et al. | |
| 2011/0004076 A1 | 1/2011 | Janna et al. | |
| 2013/0018440 A1 | 1/2013 | Chow et al. | |
| 2013/0261703 A1 | 10/2013 | Chow et al. | |
| 2014/0276048 A1 | 9/2014 | Kiley et al. | |
| 2014/0350348 A1 | 11/2014 | Tee et al. | |
| 2016/0017268 A1 | 1/2016 | Kim et al. | |
| 2016/0030757 A1* | 2/2016 | Jacobson | A61N 1/372 607/4 |
| 2016/0367186 A1 | 12/2016 | Freeman et al. | |
| 2017/0095198 A1 | 4/2017 | Towe | |
| 2017/0209094 A1 | 7/2017 | Derchak et al. | |
| 2018/0192941 A1 | 7/2018 | Annoni et al. | |
| 2018/0358119 A1 | 12/2018 | Bhushan et al. | |
| 2019/0021692 A1 | 1/2019 | Utsugida et al. | |
| 2019/0223782 A1 | 7/2019 | Wen et al. | |
| 2019/0229770 A1* | 7/2019 | Khaleghi | H04B 5/0037 |
| 2019/0254565 A1 | 8/2019 | Toth et al. | |
| 2020/0253578 A1 | 8/2020 | Chae et al. | |
| 2020/0289002 A1 | 9/2020 | Chae et al. | |
| 2020/0309612 A1 | 10/2020 | Liu et al. | |
| 2021/0052225 A1 | 2/2021 | Shetty et al. | |

FOREIGN PATENT DOCUMENTS

| | | | |
|---|---|---|---|
| WO | 2014144219 A1 | 9/2014 | |
| WO | 2015191600 A1 | 12/2015 | |
| WO | 2018011235 A1 | 1/2018 | |
| WO | WO-2018011235 A1 * | 1/2018 | H04B 5/0037 |

OTHER PUBLICATIONS

Prinzen, Frits W., Relation Between the Pacing Induced Sequence of Activation and Left Ventricular Pump Function in Animals, Journal of Pacing and Clinical Electrophysiology, p. 484-98, Apr. 2002.

De Cock, C.C., Comparison of the haemodynamic effects of right ventricular outflow-tract pacing with right ventricular apex pacing, Europace, p. 275-278, Jul. 2003.

Leclercq, C., Comparative effects of permanent biventricular and right-univentricular pacing in heart failure patients with chronic atrial fibrillation, European Heart Journal, p. 1780-1787, Nov. 2002.

YY, Yinghong, Biventricular mechanical asynchrony predicts hemodynamic effect of uni- and biventricular pacing, AJP Heart Circ Physiol, p. H2788-2796, Dec. 2003.

Knops, Reinoud, Chronic Performance of a Leadless Cardiac Pacemaker, Journal of the American College of Cardiology, p. 1497-1504, Apr. 21, 2015.

Reddy, Vivek, Cardiac Resynchronization Therapy with Wireless Left Ventricular Endocardial Pacing, Journal of the American College of Cardiology, p. 2119-2129, May 2, 2017.

Liu, Shiyi, Wireless Passive Stimulation of Engineered Cardiac Tissues, ACS Sensors, p. 1006-12, 2017.

Schwerdt, Helen N., Analysis of Electromagnetic Fields Induced in Operation of a Wireless Fully Passive Backscattering Neurorecording Microsystem in Emulated Human Head Tissue, IEEE Transactions on Microwave Theory and Techniques, p. 2170-2176, May 2013.

Schwerdt, Helen N., A Fully Passive Wireless Microsystem for Recording of Neuropotentials Using RF BackScattering Methods, Journal of Microelectromechanical Systems, p. 1119-1130, Oct. 2011.

Schwerdt, Helen N., A fully Passive Wireless Backscattering Neurorecording Microsystem Embedded in Dispersive Human-Head Phantom Medium, IEEE Electron Device Letters, p. 908-910, Jun. 2012.

Ito, Koichi, Development and Characteristics of a Biological Tissue-Equivalent Phantom for Microwaves, Electronics and Communications in Japan, p. 67-77, 2001.

Ovadia, Marc, The Electrode-Tissue Interface in Living Heart: Equivalent Circuit as a Function of Surface Area, Electroanalysis, p. 262-272, 1998.

Means, David L., Evaluating Compliance with FCC Guidelines for Human Exposure to Radiofrequency Electromagnetic Fields, FCC Office of Technology Bulletin 65, Supplement C, p. 1-53, Jun. 2001.

Hossmann, K.A., Effects of Electromagnetic Radiation of Mobile Phones on the Central Nervous System, Bioelectromagnetics, p. 49-62, 2003.

Guy, Arthur W., Analyses of Electromagnetic Fields Induced in Biological Tissues by Thermographic Studies on Equivalent Phantom Models, IEEE Transactions on Microwave Theory and Techniques, p. 205-214, Feb. 1971.

Okano, Yoshinobu, The SAR Evaluation Method by a Combination of Thermographic Experiments and Biological Tissue-Equivalent Phantoms, IEEE Transactions on Microwave Theory and Techniques, p. 2094-2103, Nov. 2000.

Navaei, Ali, Electrically conductive hydrogel-based microtopographies for the development of organized cardiac tissues, Royal Society of Chemistry Advances, p. 3302-3312, 2017.

Navaei, Ali, Gold nanorod-incorporated gelatin-based conductive hydrogels for engineering cardiac tissue constructs, Acta Biomaterialia, p. 133-146, May 2016.

Di Verniero, Carla Andrea, In Vitro and in Vivo Pharmacodynamic Properties of Metoprolol in Fructose-fed Hypertensive Rats, Journal of Cardiovascular Pharmacology, p. 532-541, Jun. 2008.

Migrino, Raymond Q., Assessment of Segmental Myocardial Viability Using Regional 2-dimensional Strain Echocardiography, Journal of the American Society of Echocardiography, p. 342-351, Apr. 2007.

Seif-Naraghi, Sonya B., Safety and Efficacy of an Injectable Extracellular Matrix Hydrogel for Treating Myocardial Infarction, Science Translational Medicine, p. 1-10, Feb. 20, 2013.

Wang, Jianqing, FDTD calculation of whole-body average SAR in adult and child models for frequencies from 30MHz to 3 GHz, Physics in Medicine and Biology, p. 4119-4127, 2006.

Auricchio, Angelo, First-in-man implantation of leadless ultrasound-based cardiac stimulation pacing system: novel endocardial left ventricular resynchronization therapy in heart failure patients, Europace, p. 1191-1197, 2013.

(56) References Cited

OTHER PUBLICATIONS

Auricchio, Angelo, Feasibility, safety, and short-term outcome of leadless ultrasound-based endocardial left ventricular resynchronization in heart failure patients: results of the Wireless Stimulation Endocardially for CRT (WiSE-CRT) study, Europace, p. 681-688, 2014.
Zehendner, Christoph, A Simple and Novel Method to Monitor Breathing and Heart Rate in Awake and Urethane-Anesthetized Newborn Rodents, PLOS One, p. 1-9, May 2013.
Graham, Emmelyn M., Quantitative mapping of aqueous microfluidic temperature with sub-degree resolution using fluorescence lifetime imaging microscopy, Lab on a Chip, p. 1267-1273, 2010.
Abbaspour-Tamijani, A. et al., "A miniature fully-passive microwave back-scattering device for short-range telemetry of neural potentials", 30th Annual International Conference of the IEEE Engineering in Medicine and Biology Society (Vancouver, British Columbia, Canada, Aug. 20-24, 2008), pp. 129-132 <DOI:10.1.109/IEMBS.2008.4649107>.
Arfin, S. et al., "Wireless Neural Stimulation in Freely Behaving Small Animals", Journal of Neurophysiology, Jul. 2009 [available online Apr. 2009], vol. 102, No. 1, pp. 598-605 <DOI:10.1152/jn.00017.2009>.
Bers, D., "Calcium Fluxes Involved in Control of Cardiac Myocyte Contraction", Circulation Research, Aug. 2000, vol. 87, pp. 275-281 <DOI:10.1161/01.RES.87.4275>.
Chen, A. et al., "Low-voltage shockmitigated micro-electromechanical systems structure", Applied Physics Letters, May 2017, vol. 110, No. 20, pp. 201903-1-5 <DOI:10.1063/1.4983645>.
Chow, E. et al., "Implantable RF Medical Devices: The Benefits of High-Speed Communication and Much Greater Communication Distances in Biomedical Applications", IEEE Microwave Magazine, Jun. 2013, vol. 14, No. 4, pp. 64-73 <DOI:10.1109/MMM.2013.2248586>.
De Venuto, D. et al., "RFID transceiver for wireless powering brain implanted microelectrodes and backscattered neural data collection", Microelectronics Journal, Dec. 2014 [available online Sep. 2014], vol. 45, No. 12, pp. 1585-1594 <DOI:10.1016/J.MEJO.2014.08.007>.
Fregni, F. et al., "A sham-controlled, phase II trial of transcranial direct current stimulation for the treatment of central pain in traumatic spinal cord injury", Pain, May 2006 [available online Mar. 2006], vol. 122, No. 1, pp. 197-209 <DOI:10.1016/j.pain.2006.02.023>.
Harrison, R., "Designing Efficient Inductive Power Links for Implantable Devices", 2007 IEEE International Symposium on Circuits and Systems (New Orleans, Louisiana, Jun. 2007), pp. 2080-2083 <DOI:10.1109/ISCAS.2007.378508>.
Hirt, M. et al., "Functional improvement and maturation of rat and human engineered heart tissue by chronic electrical stimulation", Journal of Molecular and Cellular Cardiology, Sep. 2014 [available online May 2014], vol. 74, pp. 151-161 <DOI:10.1016/j.yjmcc.2014.05.009>.
Kampianakis, E. et al., "A dual-band wireless power transfer and backscatter communication approach for implantable neuroprosthetic devices", 2017 IEEE International Conference on RFID (Phoenix, Arizona, May 9-11, 2017), Jun. 2017, pp. 67-72 <DOI:10.1109/RFID.2017.7945589>.
Larson, P. et al., "Miniature ultrasonically powered wireless nerve cuff stimulator", 2011 5th International IEEE/EMBS Conference on Neural Engineering (Cancun, Mexico, Apr. 27-May 1, 2011), pp. 265-268 <DOI:10.1109/NER.2011.5910538>.
Lee, E. et al., "A Biomedical Implantable FES Battery-Powered Micro-Stimulator", IEEE Transactions on Circuits and Systems-I: Regular Papers, Oct. 2009 [IEEE Date of Publication: Dec. 2009], vol. 56, No. 12, pp. 2583-2596 <DOI:10.1109/TCSI.2009.2034052>.
Lee, H. et al., "A Power-Efficient Wireless System With Adaptive Supply Control for Deep Brain Stimulation", IEEE Journal of Solid-State Circuits, Sep. 2013, vol. 48, No. 9, pp. 2203-2216 <DOI:10.1109/JSSC.2013.2266862>.
Lee, S. et al., "A Low-Power Bidirectional Telemetry Device With a Near-Field Charging Feature for a Cardiac Microstimulator", IEEE Transactions on Biomedical Circuits and Systems, Apr. 2011 [IEEE Date of Publication: Aug. 2011], vol. 5, No. 4, pp. 357-367 <DOI:10.1109/TBCAS.2011.2126570>.
McDermott, H., "An advanced multiple channel cochlear implant", IEEE Transactions on Bio-medical Engineering, Jul. 1989, vol. 36, No. 7, pp. 789-797 <DOI: 10.1109/10.32112>.
Navaei, A. et al., "PNIPAAm-based biohybrid injectable hydrogel for cardiac tissue engineering", Acta Biomaterialia, Mar. 2016 [available online Dec. 2015], vol. 32, pp. 10-23 <DOI:10.1016/j.actbio.2015.12.019>.
Obeid, D. et al., "Low power microwave systems for heartbeat rate detection at 2.4, 5.8, 10 and 16 GHz", 2008 First International Symposium on Applied Sciences on Biomedical and Communication Technologies (Aalborg, Denmark, Oct. 25-28, 2008; pp. 1-5 <DOI:10.1109/isabel.2008.4712623>.
Peckham, P. et al., "Functional Electrical Stimulation for Neuromuscular Applications", Annual Review of Biomedical Engineering, Aug. 2005 [available online Mar. 2005], vol. 7, pp. 327-360 <DOI:10.1146/annurev.bioeng.6.040803.140103>.
Pfurtscheller, G. et al., "'Thought'—control of functional electrical stimulation to restore hand grasp in a patient with tetraplegia", Neuroscience Letters, Nov. 2003, vol. 351, pp. 33-36 <DOI:10.1016/s0304-3940(03)00947-9>.
Ren, H. et al., "Improved current and power density with a microscale microbial fuel cell due to a small characteristic length", Biosensors and Bioelectronics, Nov. 2014 [available online Jun. 2014], vol. 61, pp. 587-592 <DOI:10.1016/j.bios.2014.05.037>.
Schulman, J., "The Feasible FES System: Battery Powered BION Stimulator", Proceedings of the IEEE, Jul. 2008, vol. 96, No. 7, pp. 1226-1239 <DOI:10.1109/JPROC.2008.922588>.
Schwan, H. et al., "The Conductivity of Living Tissues", Annals of the New York Academy of Sciences, Aug. 1957, vol. 65, No. 6, pp. 1007-1013 <DOI:10.1111/j.1749-6632.1957.tb36701.x>.
Schwerdt, H. et al., "Preliminary thermal characterization of a fully-passive wireless backscattering neuro-recording microsystem", 2011 16th International Solid-State Sensors, IEEE Actuators and Microsystems Conference (Beijing, China, Jun. 5-9, 2011), [Date Added to IEEE Xplore: Aug. 2011], pp. 1228-1231 <DOI:10.109/transducers.2011.5969400>.
Shimada, Y. et al., "Clinical use of percutaneous intramuscular electrodes for functional electrical stimulation", Archives of Physical Medicine and Rehabilatation, Oct. 1996, vol. 77, No. 10, pp. 1014-1018 <DOI:10.1016/s0003-9993(96)90061-1>.
Smith, B. et al., "An Externally Powered, Multichannel, Implantable Stimulator for Versatile Control of Paralyzed Muscle", IEEE Transactions on Bio-medical Engineering, Jul. 1987, vol. BME-34, No. 7, pp. 499-508 <DOI:10.1109/tbme.1987.325979>.
Sun, Y. et al., "Wirelessly powered implantable pacemaker with on-chip antenna", 2017 IEEE MTT-S International Microwave Symposium (Honolulu, Hawaii, Jun. 4-9, 2017), [IEEE Date of Publication: Oct. 2017], pp. 1242-1244 <DOI:10.1109/MWSYM.2017.8058831>.
Takahashi, A. et al., "Measurement of intracellular calcium", Physiological Reviews, Oct. 1999 [available online Jan. 1999], vol. 79, No. 4, pp. 1089-1125 <DOI:10.1152/physrev.1999.79.4.1089>.
Tandon, N. et al., "Electrical stimulation systems for cardiac tissue engineering", Nature Protocols, Jan. 2009, vol. 4, No. 2, pp. 155-173 <DOI:10.1038/nprot.2008.183>.
Tandon, N. et al., "Optimization of electrical stimulation parameters for cardiac tissue engineering", Journal of Tissue Engineering and Regenerative Medicine, Jun. 2011 [available online Jan. 2011], vol. 5, No. 6, pp. e115-e125 <DOI:10.1002/term.377>.
Walter, P. et al., "Cortical activation via an implanted wireless retinal prosthesis", Investigate Ophthalmology and Visual Science, May 2005, vol. 46, No. 5, pp. 1780-1785 <DOI:10.1167/iovs.04-0924>.
Want, R., "An introduction to RFID technology", IEEE Pervasive Computing, Jan. 2006, vol. 5, No. 1, pp. 25-33 <DOI:10.1109/MPRV.2006.2>.
Wolf, P., "Thermal Considerations for the Design of an Implanted Cortical Brain—Machine Interface", In: Reichert, W.M. (Ed.),

(56) References Cited

OTHER PUBLICATIONS

"Indwelling Neural Implants: Strategies for Contending with the in Vivo Environment", CRC Press/Taylor & Francis, 2008, Chapter 3.
Yamamoto, J. et al., "Low-frequency Electric Cortical Stimulation Has an Inhibitory Effect on Epileptic Focus in Mesial Temporal Lobe Epilepsy", Epilepsia, May 2002, vol. 43, No. 5, pp. 491-495 <DOI:10.1046/i.1528-1157.2002.29001.x>.
Zealear, D. et al., "The biocompatibility, integrity, and positional stability of an injectable microstimulator for reanimation of the paralyzed larynx", IEEE Transactions on Bio-medical Engineering, Aug. 2001, vol. 48, No. 8, pp. 890-897 <DOI:10.1109/10.936365>.
Zhang, X. et al., "Working Distance Comparison of Inductive and Electromagnetic Couplings for Wireless and Passive Underwater Monitoring System of Rinsing Process in Semiconductor Facilities", IEEE Sensors Journal, May 2011 [IEEE Date of Publication: Nov. 2011], vol. 11, No. 11, pp. 2932-2939 <DOI:10.1109/JSEN.2011.2151185>.
Ziaie, B. et al., "A single-channel implantable microstimulator for functional neuromuscular stimulation", IEEE Transactions on Biomedical Engineering, Oct. 1997, vol. 44, No. 10, pp. 909-920 <DOI:10.1109/10.634643>.
U.S. Appl. No. 16/809,778, Chae et al., filed Mar. 5, 2020.
U.S. Appl. No. 16/834,726, Chae et al., filed Mar. 30, 2020.
U.S. Appl. No. 16/783,579, Chae et al., filed Feb. 6, 2020.
Berger et al., Brain mapping techniques to maximize resection, safety, and seizure control in children with Brain tumors, Neurosurgery, Nov. 1989, pp. 786-792, vol. 25 issue 5.
Berger et al., Intraoperative brain mapping techniques in neuro—oncology, Stereotactic and Functional Neurosurgery, 1992, pp. 153-161, vol. 58.
Blumcke et al., Histopathological Finding in Brain Tissue Obtained during Epilepsy Surgery, New England Journal of Medicine, 2017, pp. 1648-1656, vol. 377.
Davis, New Fibre Optic Sensor for Respiratory Monitoring, Engineering Information Abstracts (Part II), p. 122-123.
Davis et al., A new sensor for monitoring chest wall motion during high-frequency oscillatory ventilation, Medical Engineering and Physics, 1999, pp. 619-623, vol. 21.
Eseonu et al., Awake Craniotomy vs Craniotomy Under General Anesthesia for Perirolandic Gliomas: Evaluating Perioperative Complications and Extent of Resection, Neurosurgery, Sep. 2017, pp. 481-489, vol. 81 Issue 3.
Feyissa et al., High-frequency oscillations in awake patients undergoing brain tumor-related epilepsy surgery, Neurology, Mar. 2018, pp. e1119-e1125, vol. 90.
Folke et al., Critical review of non-invasive respiratory monitoring in medical care, Medical and Biological Engineering and Computing, 2003, pp. 377-383, vol. 41.
Formaggio et al., Frequency and lime-frequency analysis of intraoperative ECoG during awake brain stimulation, Frontiers in Neuroengineering, 2013, vol. 6.
Franks et al., Contactless respiration monitoring of infants, Medical and Biological Engineering, May 1976, pp. 306-312.
Kwan et al., Definition of drug resistant epilepsy: consensus proposal by the ad hoc Task Force of the ILAE Commission on Therapeutic Strategies, Epilepsia, Jun. 2010, pp. 1069-1077, vol. 51 issue 6.
Kwan et al., Early identification of refractory epilepsy, New England Journal of Medicine, Feb. 2000, pp. 314-319, vol. 342 issue 5.
Kwan et al., Erratum-Definition of drug resistant epilepsy: consensus proposal by the ad hoc Task Force of the LAE Commission on Therapeutic Strategies, Epilepsia, Sep. 2010, p. 1922, vol. 51 issue 9.
Marks et al., Aminoff's Electrodiagnosis in Clinical Neurology (6th Edition), L. Saunders Ed., Chapter 7—Invasive Clinical Neurophysiology in Epilepsy and Movement Disorders, 2012.
Miller et al., Standardisation of sprirometry, European Respiratory Journal, 2005, pp. 319-338, vol. 26 No. 2.

Nakajima et al., Monitoring of heart and respiratory rates by photoplethysmography using a digital filtering technique, Medical Engineering and Physics, 1996, pp. 365-372, vol. 18 No. 5.
Nilsson et al., Monitoring of Respiratory Rate in Postoperative Care Using a New Photoplethysmographic technique, Journal of Clinical Monitoring and Computing, 2000, pp. 309-315, vol. 16 No. 4.
Niosh Spirometry Training Guide, Dec. 1, 2003, pp. 1-257, Universities Occupational Safety and Health Educational Resource Center and Centers for Disease Control and Prevention National Institute for Occupational Safety and Health.
Piezo Film Sensors Technical Manual, Apr. 1999, pp. 1-89, Measurement Specialties, Inc.
Radioactive Consumer Products, Glossy Paper, www.orau.org/PTP/collection/consumer/o20products/magazines.htm <http://www.orau.org/PTP/collection/consumer%22/o20products/magazines.htm>, 2009, pp. 1-2.
Se Dong Min et al., A study on a non-contacting respiration signal monitoring system using Doppler ultrasound, Medical and Biological Engineering and Computing, Nov. 2007, pp. 1113-1119, vol. 45 issue 11.
Semmes et al., Subjective and Objective Measurement of Tidal Volume in Critically Ill Patients, Chest Journal, May 1985, pp. 577-579, vol. 87 issue 5, Official Publication of the American College of Chest Physicians.
Siew-Mooi Ching et al., Detection of airflow limitation using a handheld spirometer in a primary care selling, Respirology, Apr. 7, 2014, pp. 689-693, vol. 19.
Simmons, Inside Laser Printer Toner: Wax, Static, Lois of Plastic, Mar. 23, 2015, www.wired.com/2015/03/hals-inside-prinler-loner/.
Voorhies et al., Techniques for placement of grid and strip electrodes for intracranial epilepsy surgery monitoring: Pearls and pitfalls, Surgical Neurology International, 2013, vol. 4.
Wade, Movements of the Thoracic Cage and Diaphragm in Respiration, The Journal of Physiology, May 28, 1952, pp. 183-212, vol. 124 No. 2.
Wehrle et al., A fibre optic Bragg grating strain sensor for monitoring ventilatory movements, Measurement Science and Technology, 2001, pp. 805-809, vol. 12 No. 7.
Wyler et al., Subdural strip electrodes for localizing epileptogenic foci, Journal of Neurosurgery, 1984, pp. 1195-1200, vol. 60.
Bashirullah, Wireless Implants, IEEE Microwave Magazine, Dec. 2010, pp. S14-S23, vol. 11, issue No. 7.
Chen, A. et al., "Wireless Wearable Ultrasound Sensor on a Paper Substrate to Characterize Respiratory Behavior," ACS Sensors, Mar. 2019, vol. 4, No. 4, pp. 944-952 <DOI:10.1021/acssensors.9b00043>.
Cop, W., "Methods and Devices Used in Ventilatory Monitoring", Encyclopedia of Medical Devices and Instrumentation, 1988, vol. 4, pp. 2870-2877.
Guder, F. et al., "Paper-Based Electrical Respiration Sensor," Angewandte Chemie International Edition, May 2016 [available online Apr. 2016], vol. 55, No. 19, pp. 5727-5732 <DOI:10.1002/anie.201511805>.
Guin, P. et al., "Design of efficient loadcell for measurement of mechanical impact by piezoelectric PVDF film sensor," AIP Advances, Sep. 2016, vol. 6, No. 9, article No. 095122, 5 pages <DOI:10.1063/1.4964148>.
Harris. G. et al., "The impact of piezoelectric PVDF on medical ultrasound exposure measurements, standards, and regulations," IEEE transactions on ultrasonics, ferroelectrics, and frequency control, Nov. 2000, vol. 47, No. 6, pp. 1321-1335 <DOI:10.1109/58.883521>.
Jow et al., Design and Optimization of Printed Spiral Coils for Efficient Transcutaneous Inductive Power Transmission, IEEE Transactions on Biomedical Circuits and Systems, Sep. 2007, pp. 193-202, vol. 1, issue No. 3.
Magori, V. et al., "Ultrasonic sensors in air," Ultrasonics Symposium (Oct. 31-Nov. 3, 1994), 1994, vol. 1, pp. 471-481.
O'Reilly, M. et al., "A PVDF receiver for ultrasound monitoring of transcranial focused ultrasound therapy," IEEE Transactions on Biomedical Engineering, Sep. 2010 [IEEE date of publication: May 2010], vol. 57, No. 9, pp. 2286-2294 <DOI: 10.1109/TBME.2010.2050483>.

(56) References Cited

OTHER PUBLICATIONS

Raboel et al., Intracranial Pressure Monitoring: Invasive versus Non-Invasive Methods—A Review, Critical Care Research and Practice; vol. 2012 Article ID 950393, Accepted Mar. 27, 2012.

Ramrakhyani et al., Design and Optimization of Resonance-Based Efficient Wireless Power Delivery Systems for Biomedical Implants, IEEE Transactions on Biomedical Circuits and Systems, Feb. 2011 [IEEE publication date: Oct. 2010], pp. 48-63, vol. 5, issue No. 1.

Ramrakhyani et al., On the Design of Efficient Multi-Coil Telemetry System for Biomedical Implants, IEEE Transactions on Biomedical Circuits and Systems, Feb. 2013 [IEEE publication date Apr. 2012], pp. 11-23, vol. 7, issue No. 1.

Seo, M. et al., "A simple breathing rate-sensing method exploiting a temporarily condensed water layer formed on an oxidized surface," Applied Physics Letters, Feb. 2015, vol. 106, No. 5, article No. 053701, 4 pages <DOI:10.1063/1.4906815>.

Wansch, Small antennas for wireless micro-systems, Active and Passive Electronic Components, 2002, pp. 71-82, vol. 25.

Yu, Y. et al., "Wrinkled nitrile rubber films for stretchable and ultra-sensitive respiration sensors," Extreme Mechanics Letters, Feb. 2017 [available online Dec. 2016], vol. 11, pp. 128-136 <DOI:10.1016/j.eml.2016.12.003>.

Zhang, X., et al., A wireless and passive wafer cleanliness monitoring unit via electromagnetic coupling for semicondutcor/MEMS manufacturing facilities, Sensors and Actuators A: Physical, Nov. 2011, pp. 414-420, vol. 171, issue No. 2.

\* cited by examiner

WIRELESS CARDIAC PACE MAKING

CROSS-REFERENCE TO RELATED APPLICATIONS

This application claims priority to U.S. provisional application 62/690,789, which was filed on Jun. 27, 2018, and is entitled Wireless Fully-Passive Pacemaker. The '789 application is incorporated in its entirety, by reference, into this application.

This invention was made with government support under 1344928 and 1734806 awarded by the National Science Foundation. The government has certain rights in the invention.

TECHNICAL FIELD

This application relates generally to systems, devices, and methods involving wireless cardiac pace making. More particularly, the application relates to implantable wireless pace making systems, devices, and methods using electromagnetic waveforms to interact with subcutaneous pace making implants.

TECHNICAL BACKGROUND

Pacemakers have regularly included a subcutaneously implanted pacing module with several electrical stimulating leads emanating from the module and connected to the right ventricle of a patient's heart. The implanted pacing module is surgically positioned near the collar bone of the patient and contains circuitry and a battery to generate pacing signals to be carried by its attached stimulating leads. The stimulating leads are surgically placed and necessitate ventricular perforation to reach the target locations of the patient's heart. Over time, the battery within the implanted pacing module will drain and need to be replaced, so repeated subsequent surgical procedures are customary for extended pacemaker use. Surgical replacement of the leads may also be necessitated over extended use due to infection, loss of efficacy, and for other reasons as well. In some instances, where a patient needs a pacemaker for a short period of time, an external pacing module, with battery and circuitry, which resides outside of the body of the patient, is used. In this short-term application, the electrical stimulating leads, which are surgically placed, emerge through the skin of a patient and are physically connected to the external pacing module.

BRIEF SUMMARY

This application generally relates to systems, devices, and methods involving cardiac pace making. These may include implantable wireless pace making systems, devices, and methods using electromagnetic waveforms to interact with subcutaneous implanted sensors or stimulators or both. Embodiments may comprise wireless, miniaturized, battery-free, radiofrequency (RF) microwave activated, sensors or stimulators or integrated sensor/stimulators that may be implanted in multiple thoracic cavity locations, and may interact with a remote pace making control-module. During use, these control-modules may be located outside the body of a patient and may also be subcutaneously located inside of a patient. Exemplary pace making control-modules may read information obtained via backscattering from a plurality of implanted sensors and may generate RF microwave, or other frequency, pulses to activate electrodes of implanted stimulators. In embodiments, the sensors and stimulators may reside in a shared implant, e.g., a Micro-Electromechanical System (MEMS), however, embodiments may also have separate sensor implants and stimulator implants. Implants of embodiments may be considered MEMS but may also have other circuit topologies as well.

In embodiments, implants may interact with one or more control-modules where these control-modules operate individually or in combination to interpret reflected waves or other communications from the implanted sensors in order to determine contemporaneous cardiac activity and to activate implanted stimulators to release pace making charges intended to improve irregular heart activity. Embodiments use of the reflected waves or other communications from the implants and tailored activation of implanted stimulators may serve to reduce heat generation and extraneous RF exposure when compared to earlier pace making systems.

Exemplary implants may be located in a user's right ventricle as well as other regions of the heart and thoracic cavity. The range of suitable implant locations may provide for tailored pacing management, tailored pacing location, and enhanced cardiac performance.

As noted above, the sensors and stimulators may be located on a single implant and may also be separate from each other. Wireless communications may be performed to and from these implants, whether separate or united. The wireless communications may be single-channel and multi-channel communications. Wireless power may be provided to the implants for purposes of generating pacing shocks for the heart. Comparatively, little to no wireless power may be transmitted for use by the implanted sensors, which operate to provide biometric signal feedback using reflective amplitude modulation. Wireless power may be tailored to provide energy for an implant stimulator to discharge a pacing shock to cardiac tissue or elsewhere in the thoracic cavity. Thus, in embodiments, reflective amplitude modulation or other reflective communication techniques may be used to obtain biometric cardiac signals from the sensor implants. These received signals may be read by a control-module or other module to make determinations as to the electro-cardiography (ECG) or other biological rhythms of a patient. When improvements to the determined rhythms are sought, RF microwave or other frequency power signals may be sent to implanted stimulators to discharge pacing shocks to target areas of the heart or other thoracic cavity area.

In embodiments, the implants may be individually addressable or otherwise located such that feedback from the implants can be attributable to a certain implant. Likewise, instructions to a stimulator can be tailored for a specific stimulator implant. Calibration steps for the implants may be performed when the implants are implanted during a surgical procedure. Calibration steps may also be performed after placement as well. Calibration may include performing pulse-ping tests where a pulse is sent and responsive pings are listened for. The time of receipt of the responsive pings may then be used to identify the order of response for a plurality of implants, e.g., with the closest implant providing the first response, the next closest implant providing the second response, etc., and the furthest implant away providing the last response.

In some embodiments a combination of implanted leads and wireless implants may also be employed. The implanted leads may serve as stimulators while the wireless implants may serve as sensors. The reverse may also exist in embodiments, and mixed combinations as well, e.g., where some wired leads are stimulators, some wired leads are sensors, some wireless implants are sensors, and some wireless implants are stimulators.

In certain embodiments, previously unsuitable regions of the thoracic cavity may be targeted for purposes of pacing. Embodiments may be advantageous by serving to reduce a need to implant pacemaker leads within cardiac chambers, as these foreign devices may lead to a host of complications such as infection, thrombosis, and tricuspid valve and ventricular perforation. Embodiments may also serve to provide pace making in regions other than the right ventricle.

Exemplary embodiments may include a cardiac pace making system having a first biocompatible implant with sensor circuitry, stimulator circuitry, an antenna, and an exposed electrode, and a control module with a remote pulse-generator. In certain instances, the sensor circuitry may be configured to receive and reflect a radiofrequency (RF) signal from the control module, and may be further configured to sense a biometric cardiac signal and modulate the sensed biometric cardiac signal onto a radio frequency-signal received from the control module. In certain instances, the stimulator circuitry may be configured to receive power via electromagnetic RF coupling from the control module and the antenna may be electrically connected to the sensor circuitry and the stimulator circuitry. Still further, in certain embodiments, the exposed electrode may be electrically connected to the sensor circuitry and the stimulator circuitry. In some embodiments, the system may also include a second biocompatible implant with sensor circuitry, stimulator circuitry, an antenna, and an exposed electrode and/or a third biocompatible implant with sensor circuitry, stimulator circuitry, an antenna, and an exposed electrode.

In some embodiments the first biocompatible implant, the second biocompatible implant, and/or the third biocompatible implant can share an antenna and a time delay circuit, where the time delay circuit may be composed of inductors, capacitors, and diodes. Here and in other embodiments, the control module may be configured to receive a multiplexed signal from the antenna and output a time-multiplexed multi-channel output signal.

In some embodiments, none of the implants or the control module may comprise a battery. And in some embodiments, the first biocompatible implant may comprise a photodiode and a varactor and the control module may be configured to receive backscattered electromagnetic (EM) waves from the first biocompatible implant when the photodiode is active and when the photodiode is not active and to extract an ECG signal from the received backscattered EM waves. Embodiments may also comprise a control module that is not physically connected to the first biocompatible implant. Also, in embodiments, the sensor circuitry may be further configured to sense a biometric cardiac signal and amplitude modulate the sensed biometric cardiac signal onto a radio frequency-signal received from the control module. Still further, in some embodiments, a fourth biocompatible implant may be present and this fourth biocompatible implant may comprise a photodiode and a varactor and the control module may be configured to receive backscattered electromagnetic (EM) waves from the fourth biocompatible implant when the photodiode is active and when the photodiode is not active and to extract an ECG signal from the received backscattered EM waves. And, in some embodiments, the first biocompatible implant or other biocompatible implants may comprise a flexible substrate. Still other configurations of embodiments are explained throughout and claimed below, and may also be present in embodiments.

Various features, steps, processes, components, and subcomponents, as may be employed in embodiments, are provided herein. These features, steps, processes, components, subcomponents, partial steps, systems, devices, etc. may be adjusted, combined and modified in various fashions and various ways among and between the teachings and figures provided herein, as well as in other ways not specifically described herein but consistent with the teachings and discussion of this disclosure.

DETAILED DESCRIPTION

Figure 1:
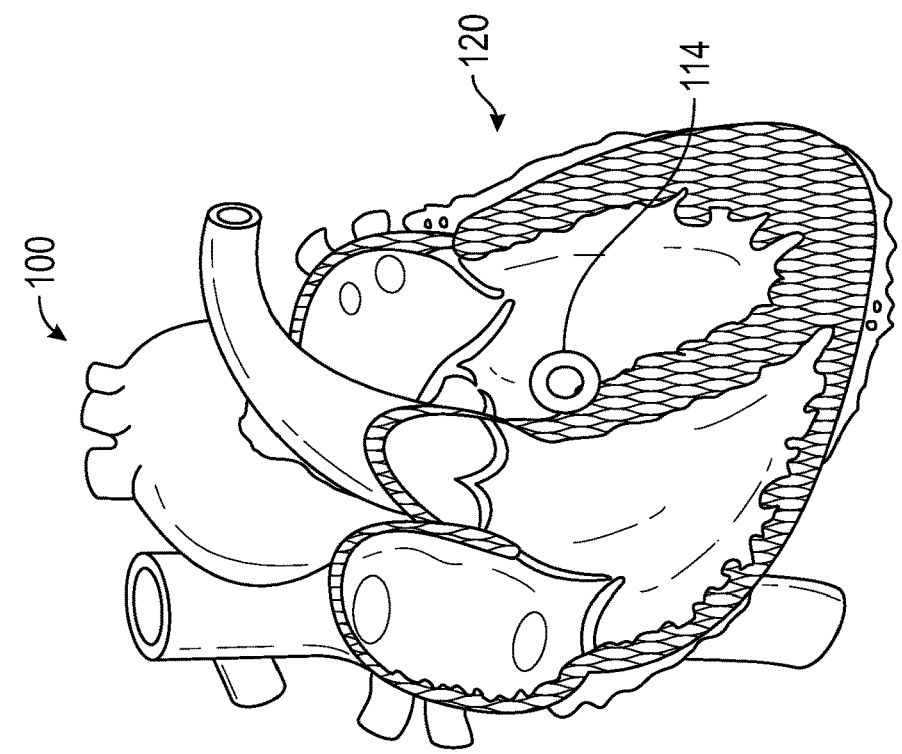
FIG. 1 illustrates outside and sectioned views of a human heart with implants and a remote pulse generator, as may be employed in embodiments.
Figure 1:
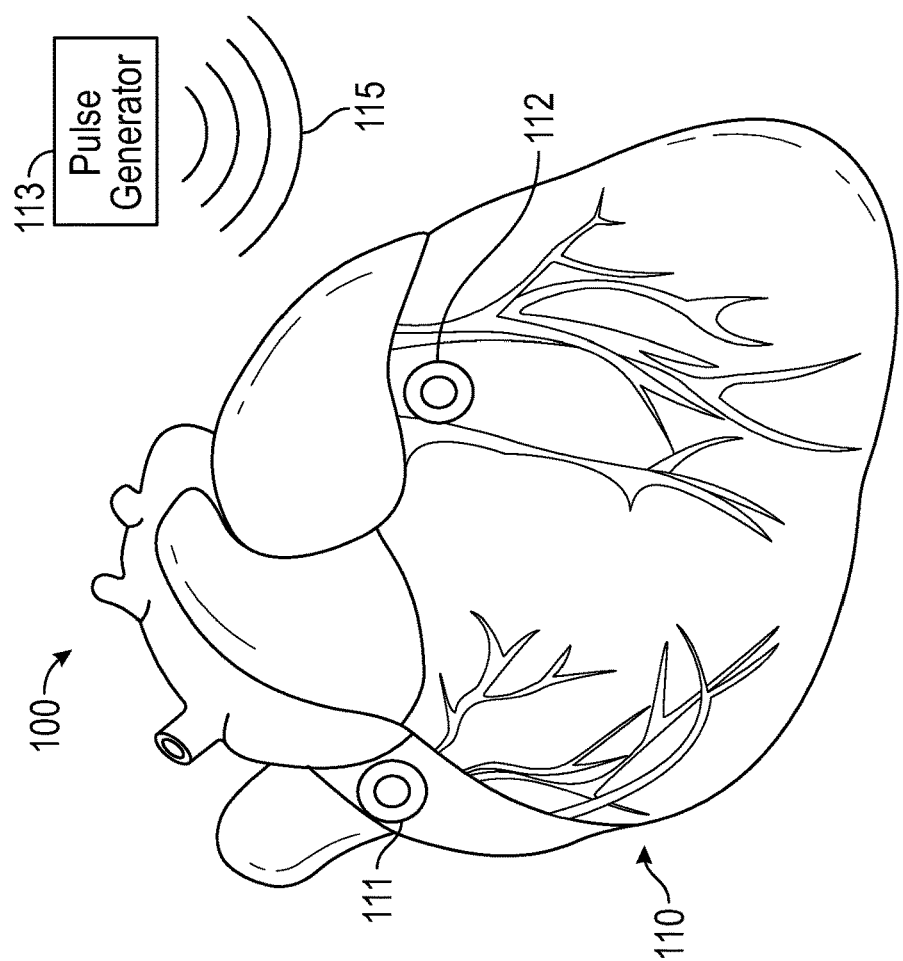

This application relates generally to systems, devices, and methods involving wireless cardiac pace making. Embodiments may include implants that can serve to sense cardiac activity, and stimulators that can serve to improve cardiac activity. One or more control-modules may be used to communicate with and provide management of the operation of the sensors and the stimulators. Wireless communication techniques may be employed to and from the implants and control modules.

Embodiments may serve, for example, to pace the left ventricle of the heart of a user and may minimize or avoid use of embedded trace wires that penetrate through ventricular walls of the heart. The pacing may be conducted using electromagnetic signals for power and communications. Implanted stimulators may be positioned around the surface of the heart, within or outside of the pericardium. In embodiments, the absence of power leads to the implants may serve to allow more suitable placement of the implantable stimulators around the heart. Accordingly, the implanted stimulators may be positioned around the heart in previously unfeasible locations. These locations may include the epicardium and the endocardium. These stimulators may be positioned using a cannula or other minimally invasive placement device, and may be positioned using more invasive techniques as well. The implants may be read and controlled using electromagnetic waveforms from a remote control-module. The remote control-module and implants may each serve as parts of a transmitter and receiver system providing pace making control of the heart of a patient.

One, two, three, four or more implanted sensors may be employed in embodiments. These implanted sensors may be passive in that they receive electromagnetic signals from a control-module and reflect back wireless communications to the remote control-module. This reflection may comprise an amplitude modulated signal to be demodulated by the receiving control-module or other system component. Implanted stimulators of embodiments may also be partially or fully powered via wireless signals from the remote control-module or other remote power source. The wireless power signals may be electromagnetic waves in embodiments, however other powering techniques may be used in embodiments.

Implants of embodiments may be various sizes and shapes. These may include polygons having sides of approximately 0.1 cm or less to approximately 1.0 or 2.0 cm or more as well as circles having diameters of approximately 0.1 cm or less to approximately 1.0 or 2.0 cm or more. Their thickness may be uniform and may vary as well with a range of approximately 0.1 cm or less to approximately 1.0 or 2.0 cm or more. Their substrates may be flexible so as to contour or otherwise adapt to an implant location. Rigid substrates may, however, be employed in implants of embodiments. Other sizes and shapes may also be employed in embodiments. Also, implants may be passive in nature, meaning that they are not internally powered by batteries or other long-term storage devices. Design topologies do not limit embodiments from including batteries or other long-term storage devices, as well as employing capacitors or other short-term storage circuit topologies. In embodiments, implants may comprise an outer coating surrounding or partially surrounding the sensor. The coating material may be biocompatible.

In embodiments, the implants may serve as both a sensor and stimulator or may provide one of the two functions. Sub-components of the implants can include one or more antenna, sensor electronics (or sensor circuitry), and/or stimulating electronics (or stimulator circuitry). The pace making system may also include one or more control-modules. These modules may include pulse-generators that can radiate a scanning signal for the sensors to reflect back with modulated information indicative of bioactivity of the heart as well as radiate a power signal for the stimulators to generate pacing shock signals for receipt by the heart. The scanning signal can be various strengths and various frequencies. The frequency used may be two or more times greater than the frequency of the carrier signal from pulse-generator however other frequencies may be employed in embodiments. The remote pulse-generator, may, for example, radiate a 30 dMb, 2.4 GHz RF signal to the implants, and receive a 4.8 GHz (3rd-order harmonics) backscattered signal from the implanted sensors. This RF backscattering technique of embodiments can be advantageous over other wireless techniques, e.g., ultrasound, which can need a location-specific acoustic window to reach an implant. Backscattering telemetry for communication may also be advantageous in embodiments as the telemetry can avoid overheating issues associated with RF induction communications, because the backscatter effect is not used for powering the electronics of the sensor implants.

As noted, implants may be sensors, stimulators, or both, and may be designed and manufactured as fully-passive MEMS. Implants and control modules may employ a single, two, four, eight, or more channels of communication and power transmission. The multichannel operation may be carried out using time-multiplexing where implants are initially calibrated as to distance, and once calibrated, subsequently received signals may be interpreted using the anticipated lags associated with the different distances between a receiving antenna and the implants. For example, as explained in more detail below, including with respect to FIG. 4, in a 4-channel wireless array, inductors, capacitors, and diodes may be employed to construct a passive time delay network, which can propagate pulse signals along each inductor/capacitor node. As a pulse-wave passes through each node, the diode may turn on the signal pathway of each corresponding channel, enabling signal from each channel to be measured in sequence. The result may generate four different waveforms (10 MHz sine, 5 MHz sine, 10 MHz square, and 5 MHz square) to be inputted into channels 1-4 respectively. The waveforms of the output signal may show a combination of signals from channel 1 to channel 4 in a time multiplexed manner. This output signal may then be demodulated to extract the cardiac activity modulated on the responsive signal. Further detail of this resultant signal is described below, including with regard to FIG. 4.

Signal artifacts, i.e., unwanted signal noise, may be compensated for in embodiments using optical modulation. This optical modulation may include using an LED to activate portions of the implanted sensor such that reflective signals with and without cardiac modulations can be reflected by the implants. This reflection of signals with and without modulated cardiac signals allows for comparison and removal of noncardiac signals from corresponding sensors. In other words, a receiving controller can subtract a received sensor signal without cardiac modulation from a sensor signal with cardiac modulation in order to identify unwanted artifacts in the received sensors signals. These unwanted artifacts, e.g., motion, electromagnetic interferences, in-situ barriers, etc., can then be compensated for in subsequent signals received by the external controller.

Remote control-modules may offer various services and functions in embodiments. These modules may be located outside the body of a patient as well as subcutaneously. The services and functions may include interfacing with thin clients, storing data received from implants, providing a programming interface for a medical professional, interacting with other control modules, providing management and control over single implants as well as groupings of implants, providing user feedback, and receiving user controls. The remote control-modules and implants may interact with each other at a suitable distance of approximately 270 mm (or more or less). As noted above, passive multi-channel techniques may be employed between these components with RF backscattering wireless communication being used so as not to power the electronics of the sensor implant, but rather to allow bidirectional communication by reflecting the incident RF wave. In embodiments, the radiofrequency (RF) microwave pulse generator of the remote control-module may be located apart from the remote control-module and may itself by subcutaneously implanted or used as an external wearable device, as an option for cases that are not hemodynamically pacemaker dependent.

The implants and control modules may be placed by various surgical techniques, which may include endocardial implantation, via central venous or arterial approach, or epicardial implantation of implants, via ultrasound or CT guided transcutaneous approaches, via minimally invasive mediastinoscopy or during planned open-heart surgery.

Thus, embodiments may provide broad selection of cardiac regions, in addition to the left and right ventricle.

Embodiments may employ backscattering communication and powering techniques for multiple implants. For example, an electromagnetic wave may be generated outside of the body and sent to a single implant or groups of implants. The implants may receive the waves and return modified waves with information modulated on the returned waves. This receipt and return may be carried out by several implants at the same time as well as at different times. The responsive signals may be coordinated with each other, or may be independent in their timing. This may substantially lower the RF power thus reducing or avoiding local tissue heating effect.

In embodiments radio-frequency (RF) backscattering effects may be utilized to communicate with implanted sensors. Responsive signals may be collected, stored, and analyzed to construct ECG or other heart activity indicators. Corrective actions may also be taken in response to received signals. These corrective actions may include sending instructions to a pacing module or directly to implanted stimulators which may, in turn, carry out the pacing instructions via electrical stimulus of the heart.

In embodiments, backscattering may comprise modulation of a received signal by the implant sensor. In operation, the frequency of the carrier signal may be reflected substantially back at the same frequency, however the amplitude of the waveform may change and this change in amplitude may be read and interpreted to identify the heart activities. Exemplary frequencies of EM backscattering initial signal waves may be on the order of approximately 2.45 gHz. In response to these initial signals, implant embodiments may employ variable capacitor (varactor) that modulate a local low frequency biological signal, for example approximately 1.5 kHz to 3 kHz, onto the initial signal and then reflected back the low frequency biological signal with the initial signal via an external antenna of the sensor implant. This combined signal can be received and read by a control-module that can extract the low frequency biological signal from the received reflected signal.

Use of a varactor in embodiments can provide nonlinear modulation of the low frequency biological signal. As such, nonlinear behavior of the varactor contributes strong harmonics of the RF. This nonlinear varactor harmonic components can be complimentary of the harmonics of the low frequency biological signal. Second, third, and fourth harmonic components may be tested by a control-module to identify the modulated biological signal in the reflected signal.

In embodiments, multi-channel operation may be used to collect signals from the multiple implanted sensors. Time multiplexing calibration may be used to identify where responsive signals are received from. For example, when a pulse-ping is received the time in which the signals are received can be indicative as to which implant is responding. During installation a time delay may be identified for each installed sensor. For example, if five implants are placed during surgery, an EM signal at approximately 2.45 GHz may be used to calibrate each implant and the timing of receipt of a calibration signal may be used to identify each implant.

Reflected signals from a plurality of implants may be used in embodiments to reconstruct an ECG signal. In use, an EM signal at approximately 2.45 GHz may be sent and may reach implants at different times. Reflected signals may then be received at a control-module antenna. Based on the timing of receipt of the signals each specific implant signal may be identified and extracted from the received reflected signals. Harmonics of the reflected signals may be considered in order to extract the ECG signal. In other words, as noted elsewhere herein, 2nd, 3rd, and 4th level harmonics of the received reflected signal may be considered and evaluated to remove the initial carrier signal and determine the underlying biological signal modulated in the reflected signals from the sensors. In embodiments, the carrier signal frequency may be approximately one hundred times faster or more than the frequency of the biological signal.

Artifact reduction methods may be employed in embodiments to minimize artifact inclusion. Artifact reduction may include calibrating implanted sensors using infrared LED from outside the body to test responsive signals from the implants. For example, during a calibration mode, when the LED light signal is sent to the implant, all responsive signals, including the ECG may be provided by the implant. Comparatively, during a calibration mode, when the infrared LED is off, only the artifacts may be included in the responsive and not the targeted ECG. Thus, a comparison can be made to subtract out background artifacts by comparing the two signals. In short, during a calibration mode, all signals including the artifacts are collected during one testing phase and during a different testing phase only artifacts are collected. The results of these two testing phases can then be compared to identify the artifacts.

In embodiments, stimulators may be passive, and may be activated upon receipt of radio frequency (RF) microwaves. These microwaves or other powering waveform may provide power to the stimulators to allow them to deliver current as high as approximately 60 mA or more to targeted cardiac tissues. In embodiments, microwave radio frequencies can serve to eliminate the need for a bulky external inductive coil. In embodiments, the stimulators may consist of an on-board miniaturized antenna, multistage diode voltage multipliers, and an output-controlling transistor. In embodiments, the stimulator circuit topology may consume low power, e.g., less than approximately 18 mW. In embodiments, an external antenna, less than approximately 10×10× 0.9 mm$^3$, may irradiate approximately 2.4 GHz modulated RF signals to a target stimulator at a distance of up to approximately 1.2 cm. Electrical stimulation has been shown to enhance the key biological properties in cardiac cells including alignment, protein expression, and contractility. Thus, embodiments, may provide a wireless stimulator with the ability to electrically trigger synchronous contractions in cardiac cells.

Stimulator embodiments may generate a monophasic square wave pulse with relatively short duration to excite heart-tissue. The stimulating pulse frequency may be in the range of several hertz, depending on heart beating rate and the stimulating current may be approximately 60 mA or more. The circuit topology of stimulators may limit maximum power dissipation of the stimulator and the maximum allowable external RF energy employed to be within safety regulations. In embodiments, these parameters may be as follows: stimulating current greater than approximately 60 mA, frequency approximately 0.5-2 Hz, external RF power less than approximately 30 dBm, and heat dissipation less than approximately 40 mW/cm$^2$. Other parameters may also be targeted and used in embodiments.

FIG. 1 illustrates outside and sectioned views of a human heart with implants and a remote pulse generator as may be employed in embodiments. The outside view 110 of the heart shows implants 111 and 112 outside of the heart along with remote pulse generator 113. The sectioned view 120 shows an implant 114 located within the heart 100. The remote pulse generator 113 may be resident in a control-module located within or outside of the body of a patient. The electro-magnetic pulses 115 may be directed to the implants 111 or 112 as well as the implant 114. The implants 111, 112, and 114 may be combined sensor/stimulators and may use the received pulses 115 to generate electrical shocks to pace the heart 100. The implants may also reflect back the electro-magnetic pulses to provide information regarding the rhythms of the heart 100 to the control-module housing the remote pulse generator 113. While three sensor/stimulator implants 111, 112, and 114 are shown, more or fewer implants may be used in embodiments. Also, the implants may be located in different locations within and outside of the heart and may all be located within the heart or outside of the heart in embodiments.

Figure 2:
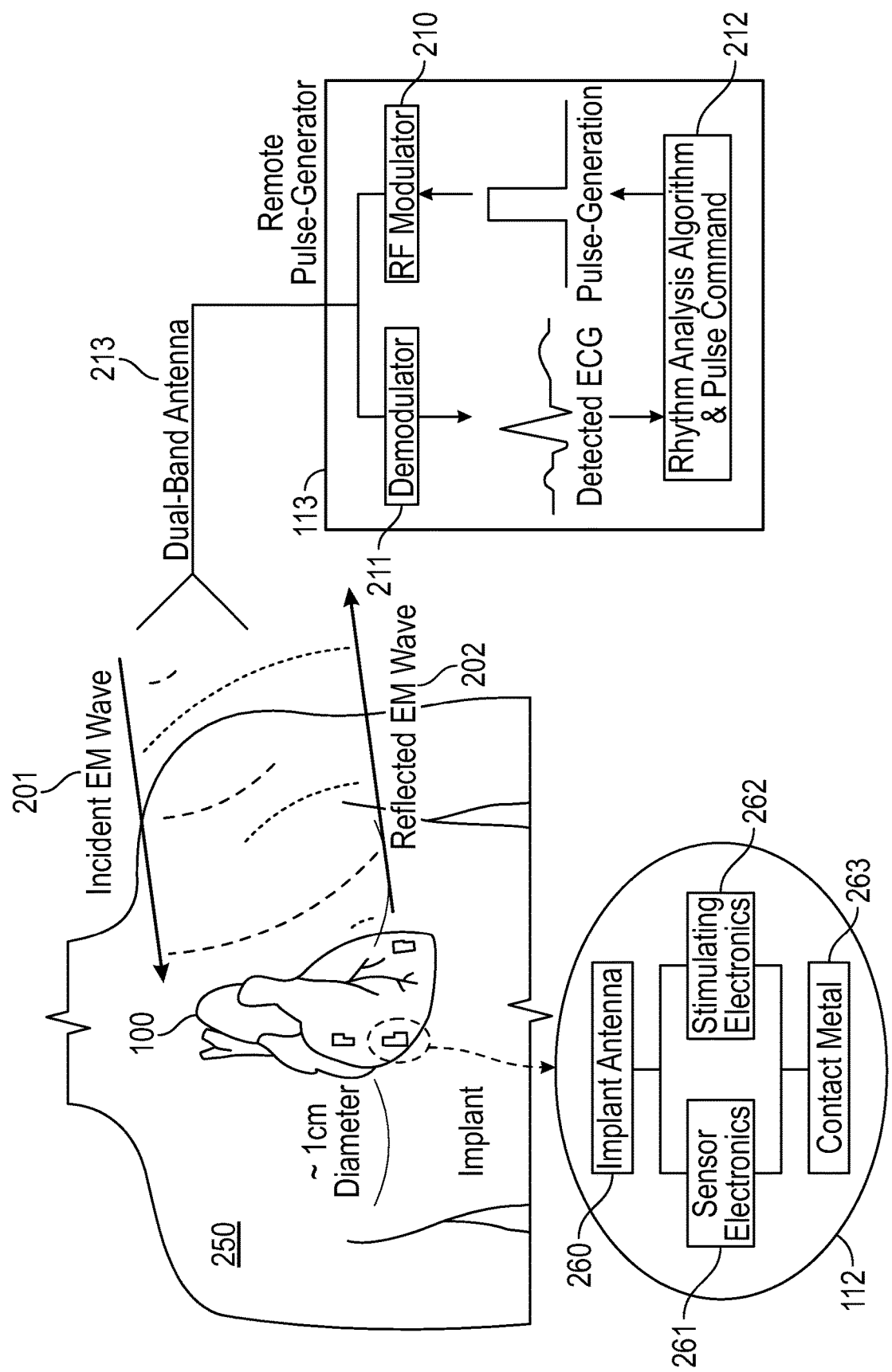
FIG. 2 illustrates a general operational activities and components of the implants and remote pulse generator of FIG. 1, as may be employed in embodiments.

FIG. 2 illustrates general operational activities and components of the implants and remote pulse generator of FIG. 1 and as may be employed in embodiments. As can be seen, implant 112 is approximately 1cm in diameter and contains an antenna 260, sensor electronics 261, stimulator electronics 262, and electrode or contact metal 263. This implant 112, like the others, is positioned in body 250 and is positioned to receive incident EM wave 201 and reflect back EM wave 202, with the reflection being carried out by sensor electronics 261. Dual-band antenna 213 is positioned to receive the reflected EM wave 202 and provide this signal to the remote pulse generator 113 of the control-module. This remote pulse-generator 113 is shown with an RF modulator 210, a demodulator 211, and a rhythm analysis algorithm and pulse control module 212. The module 212 may receive detected ECG signals from the demodulator 211 and provide command pulses to the RF modulator 210. Thus, in embodiments, button sized implants may be implanted in specific cardiac regions and may communicate with a remote pulse generator via electromagnetic (EM) backscattering effect. The implants may each send cardiac signals via its internal antenna, using EM backscattering effect, to the remote pulse-generator 113 of a remote control-module where an ECG of the heart 100 may be visualized.

The control module may manage pacing commands by deactivating them unless an elapsed cycle length exceeds pre-set thresholds to maintain minimum heart rates. When elapsed cycle lengths exceed the threshold, the pacing command produces modulated RF signals, through RF modulator 210, which may activate stimulating electronics to dispense electrical stimulation via contact metal 263 to the heart 100. As noted above, in embodiments, the proposed RF telemetry does not power electronics inside the implants, but rather, allows bi-directional communication by reflecting the incident RF wave, avoiding significant heating that traditional RF communication methods impose. Power to the electrodes may be provided using RF microwaves, which can provide power with less incident heating.

Figure 3:
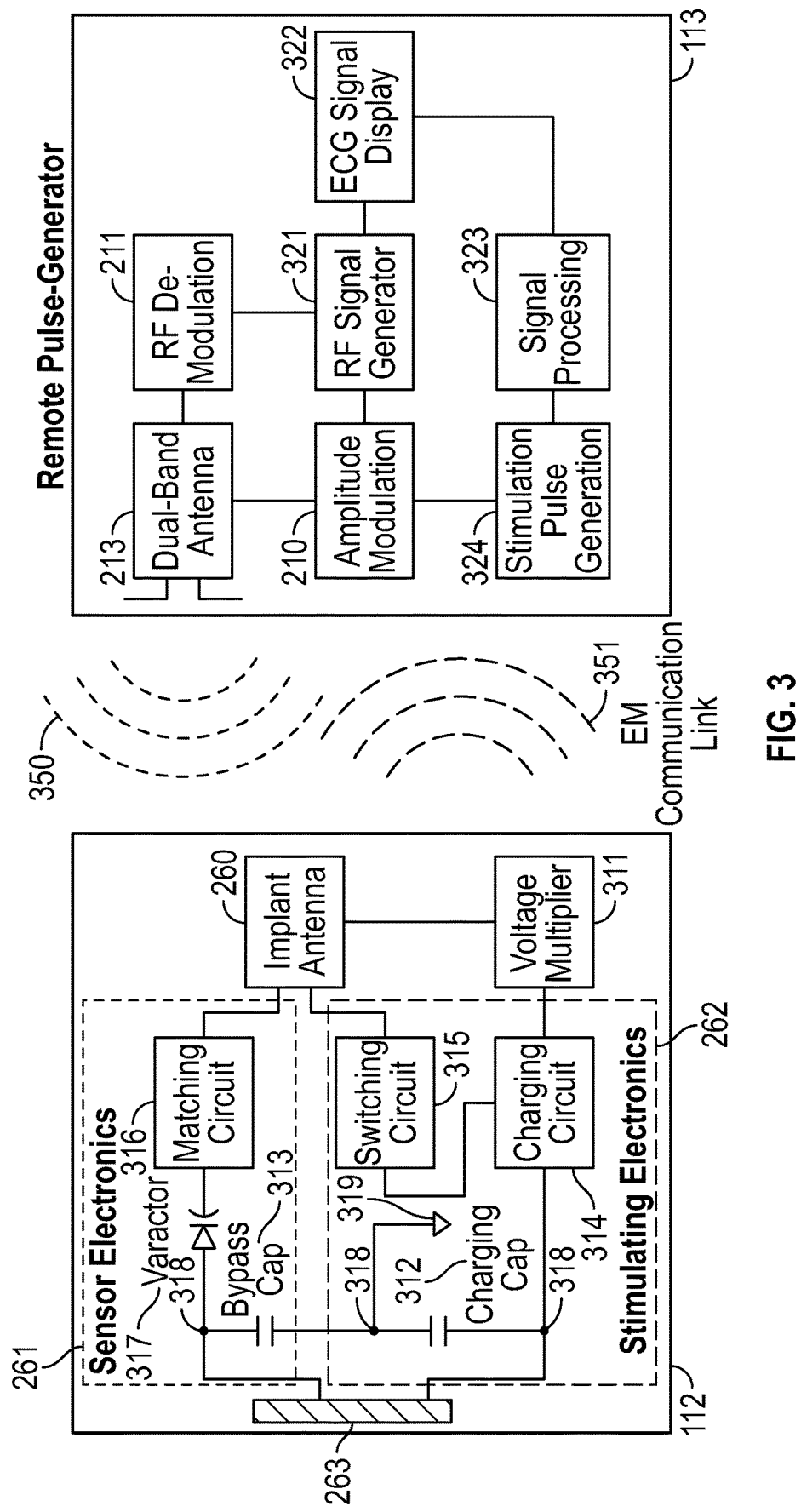
FIG. 3 illustrates a more detailed schematic of the wireless pace making system of FIG. 2, as may be employed in embodiments.

FIG. 3 illustrates a more detailed schematic of the wireless pace making system of FIG. 2, as may be employed in embodiments. An implant 112 is shown in EM communication with a remote pulse-generator 113. This implant 112 may be placed at various locations within the thoracic cavity and may communicate with a control-module containing the remote pulse-generator 113. The implant 112 is shown with sensor electronics 261, stimulating electronics 262, implant antenna 260, contact metal 263, and voltage multiplier 311. Also shown in the implant 112 are charging capacitor 312, bypass capacitor 313, charging circuit 314, switching circuit 315, matching circuit 316, varactor 317, nodes 318, and ground 319. The remote pulse generator 113 is shown with dual-band antenna 213, RF demodulator 211, RF modulator 210, RF signal generator 321, ECG signal display 322, signal processor 323, and stimulation pulse generator 324. The electromagnetic communication between the implant 112 and the remote pulse generator 113 are shown at 350 and 351. The implant 112 may be various sizes and shapes. For example, the implant may be formed on a flexible substrate with integrated circuits supported thereon. The substrate may be approximately 4×12×0.5 mm. As can be seen in FIG. 3, the contact metal 263 may serve the sensor electronics as well as the stimulating electronics in embodiments. Likewise, an implant antenna 260 may be shared by both sensor electronics 261 and stimulator electronics 262. While a combined sensor/stimulator implant is shown in FIG. 3, implants may be constructed to perform only sensing or stimulating functions. In such embodiments, the sensors and stimulators would have their own contact metals, e.g., electrodes, and antenna. As can also be seen in FIG. 3, the bi-directional RF communication does not power sensor/stimulating electronics (no power supply or power regulating elements), but utilizes backscattering effect to sense ECG and pace the heart. This unique telemetry allows substantially low RF power to communicate to minimize any heat effect. The contact metals and sensor electronics 261 can sense compound action potentials of varying intensities, including in the range of approximately 500 pVpp. The stimulating electronics 262 can generate stimulation currents of various magnitudes, including currents up to and over approximately 60 mA.

In operation, the remote pulse-generator may radiate approximately 2.4 GHz RF to the electrodes, while the generator simultaneously receives approximately 4.8 GHz (3rd-order harmonics) backscattered signal, where ECG is visualized via RF demodulator. Operating embodiments at approximately 30 dBm, as regulated by FCC, results in ~40 µV MDS with over approximately 200 mm wireless distance. Also, an approximately 30 dBm RF may be amplitude modulated to control the pacing pulses at the electrodes. The pulse generation may be controlled by having an ECG signal fed to a signal processing algorithm that detects the QRS feature. The algorithm may generate the stimulating pulse, approximately 3-5 milli-sec width, at a set interval, such as 1 sec. When a normal QRS feature is detected, the timer of the algorithm may be reset and no pulse may be generated. When no intrinsic cardiac signal is detected for a threshold, the algorithm may generate a pacing pulse, which controls the charging capacitor of the electrode to discharge, pacing the cardiac tissue. The wireless implant may be fabricated on a biocompatible flexible substrate, polyimide, by MEMS technology. In use, embodiments may function to detect signals as low as approximately 140 µV, even when input impedance is as high as approximately 100 kOhm, which is suitable for normal ECG signal, which can be ~5-10 mV at the surface of heart.

Figure 4:
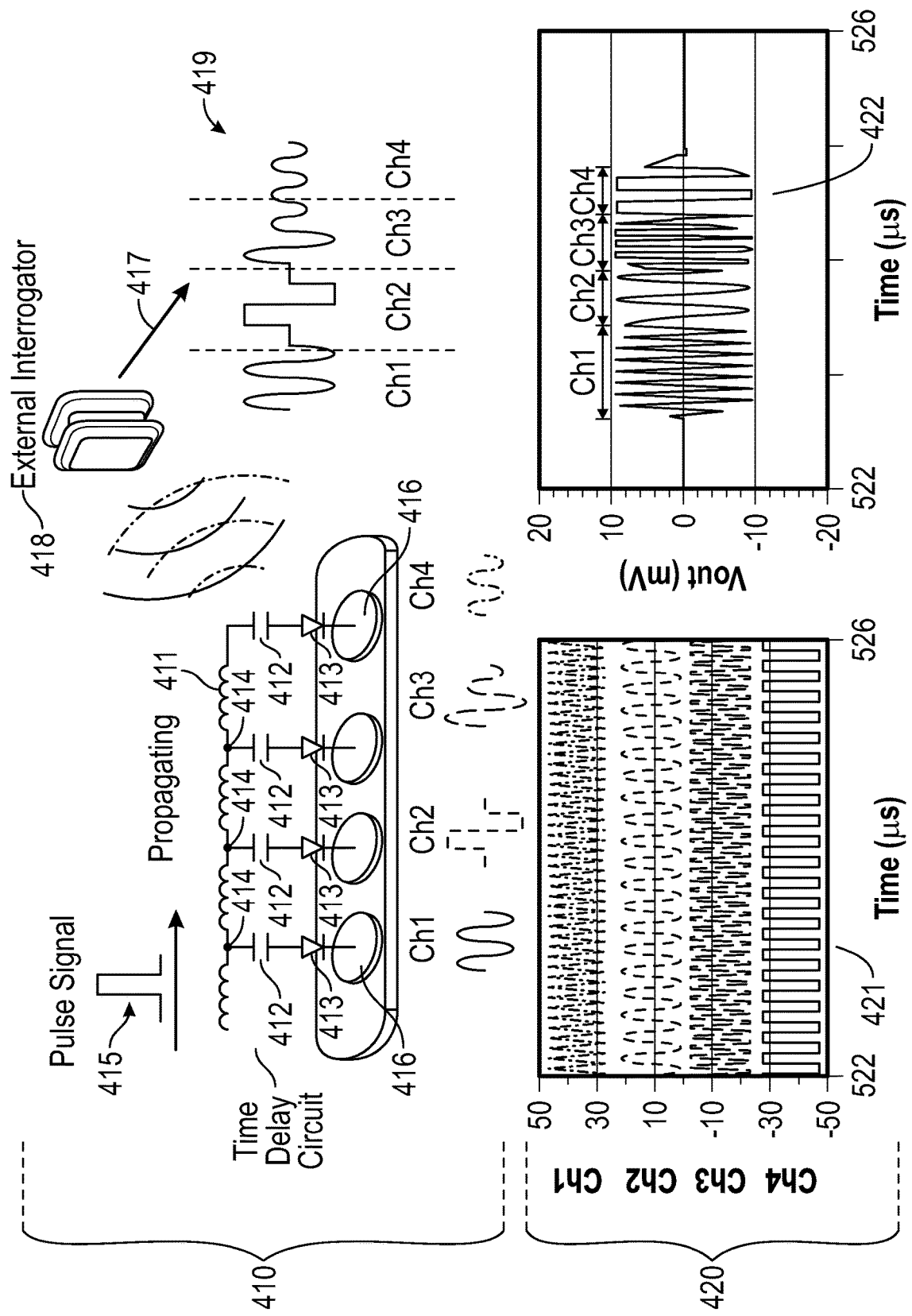
FIG. 4 illustrates features of multi-channel communications, as may be employed in embodiments.

FIG. 4 illustrates features of multi-channel communications as may be employed in wireless pace-making systems of embodiments. FIG. 4 at 410 illustrates the topology of a 4-channel wireless array of multiple implants or multiple sensor circuits that may share a single antenna. Embodiments may use a single antenna for multiple sensor circuits to reduce the EM communication footprint and allow for more centralized EM communication areas of a user. In other words, by using a single antenna for multiple sensor circuits the number of communication points may be reduced without a likewise reduction in the number of sensing locations.

As can be seen in FIG. 4, inductors 411, capacitors 412, and diodes 413 are connected so as to construct a passive time delay network for the multiple implants, which propagates pulse signal along each of the inductor/capacitor nodes 414. As the pulse wave 415 passes through each node 414, each corresponding diode 413 turns on the signal pathway of each corresponding channel 416, enabling signal from each channel 416, each reflecting output of a single implant, to be measured in sequence. Thus, embodiments may comprise a time delay circuit, composed of inductors, capacitors, and diodes, constructed to deliver a propagating pulse signal which alternately turns on channels 1-4 at different times. The output signal 417 of external interrogator 418 contains the waveform 419 of all channels, indicative of outputs from multiple implant sensors, in the corresponding time sequence.

FIG. 4 at 420 shows an exemplary result of 4 channel signal recording. In this example, input signals 421 of each channel are shown at 20 mVpp with different waveforms and Output signal 422 illustrates a combination of the 4-channel signal in a time multiplexed manner. Thus, in FIG. 4 at 420 four different waveforms (10 MHz sine, 5 MHz sine, 10 MHz square, and 5 MHz square) are inputted to channels 1-4 respectively and the waveform of output signal 422 shows a combination of signals from channel 1 to channel 4, which can correspond to sensed signals from sensor circuits 1-4, in a time multiplexed manner. When lower frequencies are employed in embodiments, on the order of less than approximately 1000 Hz for example, an eight-channel time multiplexed time delay circuit may be better suited in order to identify the individual channels from the combined output signal and the underlying sensor circuits.

Figure 5:
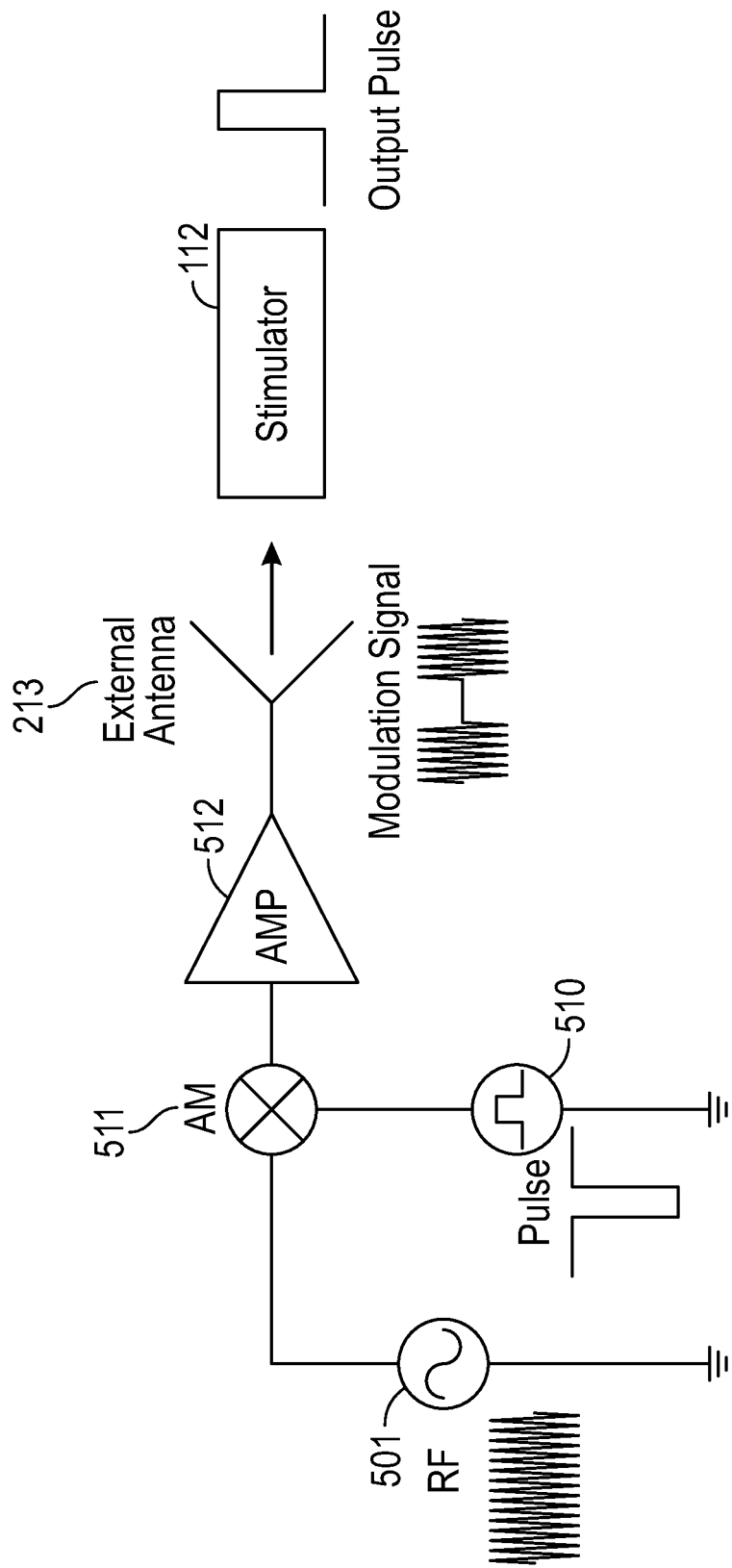
FIG. 5 illustrates exemplary topology and operation of control-module transmission, as may be employed in embodiments.

FIG. 5 illustrates exemplary topology and operation of control-module transmission as may be employed in embodiments. In operation, an inverted pulse 510 modulates 2.4 GHz RF carrier 501 through amplitude modulation 511. The modulated signal may be amplified, then radiated from the external antenna 213. The frequency and pulse width of the inverted pulse may be set to be approximately 0.5 2 Hz and approximately 2 ms, whereas the high/low levels of the inverted pulse may be set at approximately 2.8 and approximately 0 V, respectively, other settings may also be used. The pulse 510 and RF carrier 501 may be generated by an arbitrary waveform (e.g., Agilent 33250A) and RF signal generators (e.g., Agilent E4432B), respectively. Modulation depth of RF generator may be set to approximately 32.5%. The modulated signal may be amplified by a low-noise power amplifier 512 (e.g., MPA-24-20, RF bay). The radiating external antenna may be a 2.4 GHz 10×10 mm2 ceramic chip antenna (e.g., A10194, Antenova). Maximum power at the RF signal generator may be set to be approximately 30 dBm, guided by Federal Communication Commission (FCC) regulation. The actual radiating power from the external antenna may be less than approximately 30 dBm.

Figure 6:
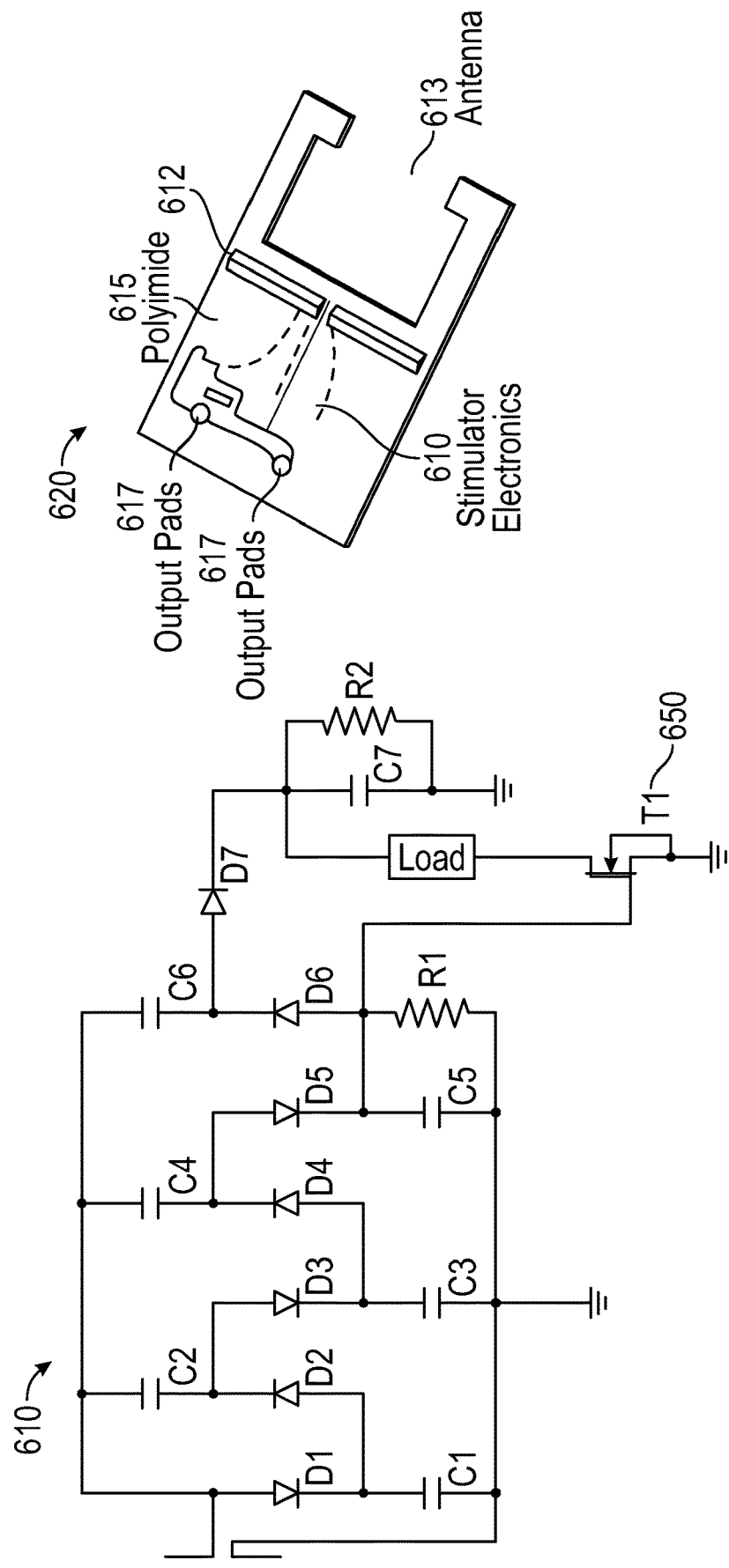
FIG. 6 shows circuit topology and a perspective view of a passive wireless stimulator, including the antenna and circuits, as may be employed in embodiments.

FIG. 6 shows circuit topology 610 and a perspective view 620 of a passive wireless stimulator 612, including the antenna 613 and circuits 610, as may be employed in embodiments. The wireless stimulation circuit 610 is shown fabricated on a 25-m-thick polyimide substrate. The metal traces are formed by a thin chrome-gold-chrome lm (Cr/Au/Cr, 20/200/20 nm). Discrete components are mounted using biocompatible conductive sliver paste (ED21TDCSMED, Master-bond). The total size of the stimulator 620 is 25×42×1.6 mm3, including the on-board antenna 613. The passive stimulator circuit 610 utilizes multistage diode voltage multipliers D1-D6 to accumulate electric charges. Only one active component transistor 650 (p-channel MOSFET) is used as a switch to control the output. The circuit 610 operates at two states. In the charging state, the voltage accumulated on resistor C5 and C7 is almost equal; the gate-source voltage of the pMOS is near zero (Vgs 0), turning "off" the transistor diodes until the voltage across C7 reaches 8-20 V. In the discharging state, the transistor 650 turns "on", and C7 discharges its accumulated charges. The stimulating current is determined by the voltage across C7 and the resistance of the cardiac tissue. The "on" state of the circuits may be controlled to maintain only a few milliseconds at a frequency of only a few hertz. The total power consumption of the circuits may be mainly contributed by the heat dissipation of resistors R1 and R2, which are 22 and 300 k, respectively, contributing approximately 2.9 18 mW. In embodiments, settings may include, 2.9 mW to excite cardiac tissue contraction. It should be noted that increasing the values of R1 and R2 can significantly decrease the power consumption of the stimulator. For example, increasing R1 and R2 by 10 times will reduce to a power consumption of merely 1.8 mW. Also labelled are output pads 617 and polymide 615.

States of the circuit 610 may be controlled by an external RF interrogator. Two methods for wireless power delivery may be employed: inductive coupling and electromagnetic (RF) coupling. Inductive coupling can perform better in close distance and high-power requirement settings whereas RF coupling can be better suited for power-limited, long-range applications. Thus, at a given transmitting power, RF coupling delivers higher DC voltage than inductive coupling does. Additionally, inductive coupling features that the external coil scales dramatically large as the working distance increases, whereas RF coupling demonstrates that the size of the external antenna is rather independent upon the working distance. Given these parameters, embodiments may employ RF coupling for stimulating electronic circuitry and pulsing operations. Embodiments may employ a 2.45 GHz RF carrier frequency considering the balance between the size of the on-board antenna and the skin-depth penetration into the body. A high frequency RF may be employed to minimize the size of antenna but a high frequency RF can result in a significant loss within tissues. PDMS may be employed for the antenna dielectric material as PDMS may be suitably flexible and can be a biocompatible material with a relatively low dielectric loss (=0.0015-0.0035).

Figure 7:
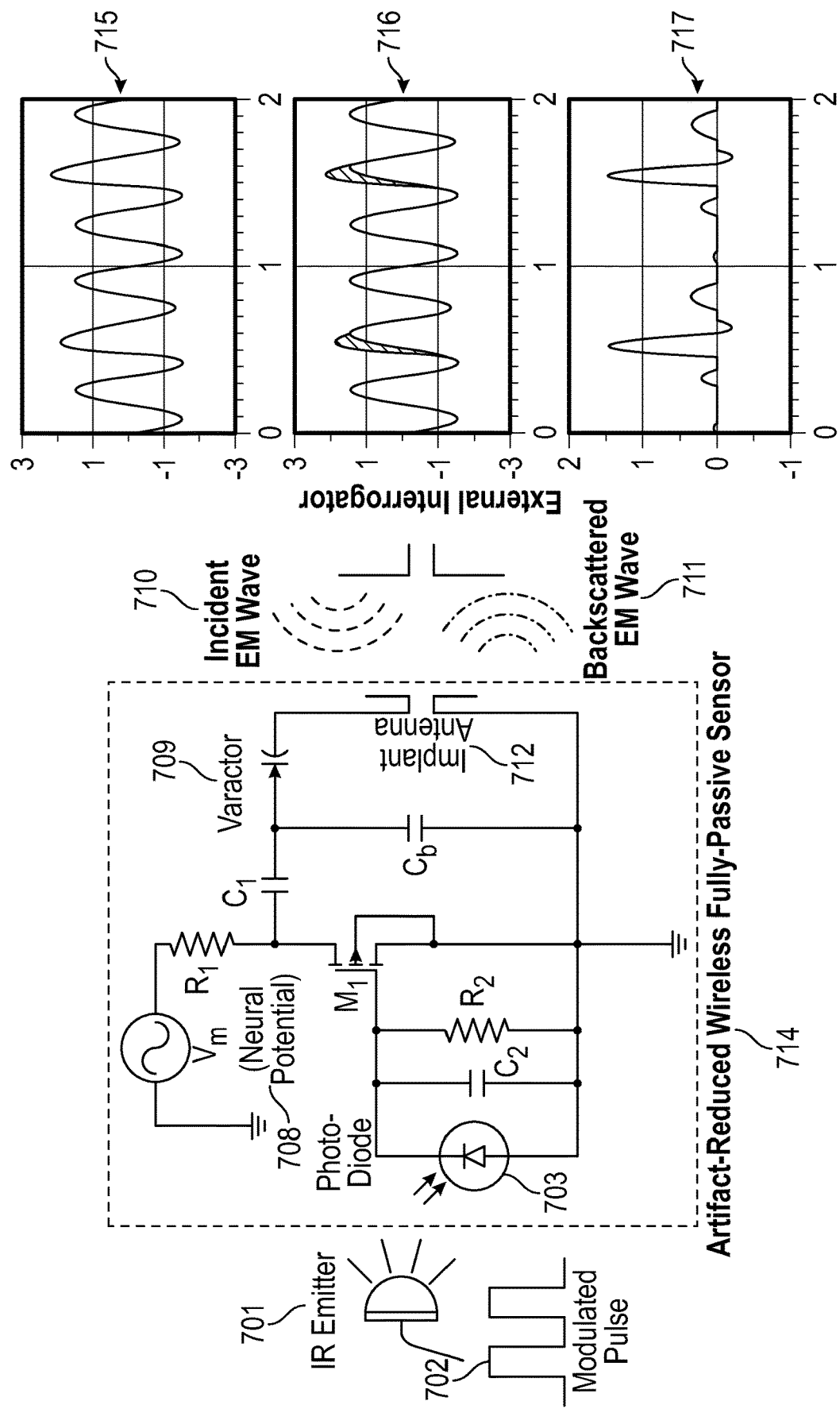
FIG. 7 illustrates an exemplary circuit and operational activities regarding artifact reduction, as may be employed in embodiments.

An exemplary method of artifact reduction is provided in FIG. 7. As can be seen in the Figure, artifact reduction of embodiments, may use optical modulation. The optical modulation may use infrared frequencies as these frequencies can have favorable properties for reaching implants located within the body. In use, an external IR emitter may radiate a beam of IR light whose intensity is modulated by an external pulse wave. A photodiode on a receiving implant may detect the IR light and output a corresponding pulse wave to the gate and source terminal of a NMOS transistor or other suitable circuit topology. The gate-source voltage of the transistor controls the resistance between its drain and source. In so doing, the pulse wave generated by the photodiode repetitively switches the transistor between high and low resistance states. At high resistance state, the neural signal is fed to a varactor and the implant transmits the signal, with artifacts, via RF backscattering to the external interrogator or other receiving module. At low resistance state, however, the transistor shorts the neural signal to ground, and the implant starts to transmit the baseline, containing only artifacts, to the interrogator or other receiving module. By subtracting the baseline, containing only artifacts, from the combined signal, an artifact-free signal can be obtained with significantly-improved signal integrity.

As to the frequency domain, in embodiments, the frequency of the pulse wave may be much higher than a neural signal, in so doing the on-off switching effectively up-converts the neural signal to a higher frequency band, allowing effective elimination of artifacts from the combined signal.

FIG. 7 also shows the simulation result of artifact reduction on a 1 Hz 1.6 mVpp emulated ECG signal. For simplicity, in this example, a 3 Hz 3 mVpp sine wave is introduced as artifacts. In practice, the artifacts may hold much more complicated wave forms. As can be seen, ECG is overshadowed by the artifacts and QRS features of the ECG are completely indistinguishable without artifact reduction whereas the up-converted signal can be distinguished from low frequency artifacts when artifact reduction is incorporated. The artifact-free ECG signal shows details of ECG features, e.g., PQRST waves.

FIG. 7 shows an exemplary circuit and operational activities regarding artifact reduction as may be employed in embodiments. Exemplary artifact reduction methods may employ single channel wireless fully-passive neuro-recorder. In these exemplary methods an infrared (IR) emitter 701 may be used to radiate pulse modulated IR light 702. A photodiode 703 may sense the variation of IR intensity and output a corresponding pulse wave signal, controlling the resistance of the MOS transistor, switching off/on the circuits as the pulse goes high/low level. The frequency of pulse may be much higher than a neural potential 708 bandwidth. The neural potential 708 is therefore up-converted and may be distinguished from low frequency noise and artifacts. Also labelled in FIG. 7 are the incident EM waves 710, backscattered EM waves 711, and varactor 709.

Exemplary signals 715-717 show output signals with and without artifact reduction. Signal 715 shows a target 1 Hz, 1.6 mVpp ECG signal disrupted by a 3 Hz, 3 mVpp emulated sine wave artifact. In this signal 715, without artifact reduction, the ECG waveform is overshadowed by the artifacts and QRS features are completely indistinguishable. Signal 716 shows an output signal with artifact reduction, here the up-converted signal can be clearly seen from low frequency artifacts. Signal 717 shows the extracted ECG signal, where the details of ECG features (PQRST waves) are visible. Also labelled are implant antenna 712 and sensor 714.

Figure 8:
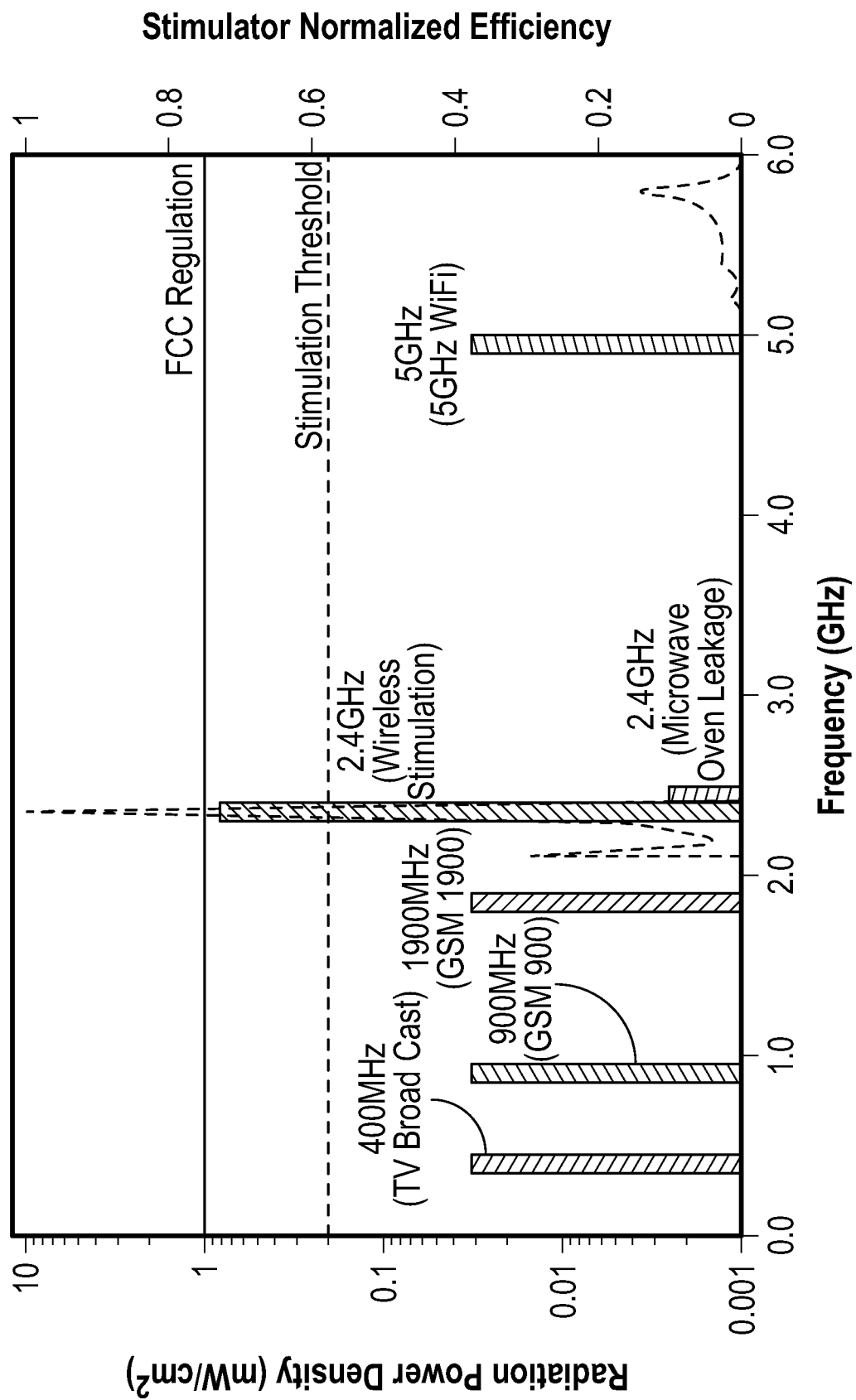
FIG. 8 illustrates potential interference from various RF interferences which may be evaluated when considering operational frequencies of embodiments.

FIG. 8 shows potential interference from various RF interferences which may be considered when considering operational frequencies of embodiments. As can be seen in FIG. 8, suitable operational frequencies are bounded by TV/cell phone tower, microwave, and WiFi frequencies. Thus, embodiments may operate with an RF of approximately 2.4 GHz and employ implant antennas optimized to receive targeted RF of approximately 2.4 GHz.

While embodiments have been illustrated herein, it is not intended to restrict or limit the scope of the appended claims to such detail. In view of the teachings in this application, additional advantages and modifications will be readily apparent to and appreciated by those having ordinary skill in the art. Accordingly, changes may be made to the above embodiments without departing from the scope of the disclosure.

Various features, steps, processes, components, and subcomponents may be employed in certain embodiments. These features, steps, processes, components, subcomponents, partial steps, systems, devices, etc. may be adjusted, combined and modified in various fashions and various ways among and between the teachings and figures provided herein, as well as in other ways not specifically described herein but consistent with the teachings and discussion of this disclosure unless otherwise indicated herein or otherwise clearly contradicted by context. All methods described herein can be performed in any suitable order unless otherwise indicated herein or otherwise clearly contradicted by context.

The terminology used herein is for the purpose of describing particular embodiments only and is not intended to be limiting. As used herein, the singular forms "a," "an" and "the" are intended to include plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The use of any and all examples, or exemplary language (e.g., "such as") provided herein, is intended merely to better illuminate and does not pose a limitation on scope unless otherwise claimed. No language in the specification should be construed as indicating any non-claimed element as essential.

As used herein, the terms "about" or "approximately" in reference to a recited numeric value, including for example, whole numbers, fractions, and/or percentages, generally indicates that the recited numeric value encompasses a range of numerical values (e.g., +/−5% to 10% of the recited value) that one of ordinary skill in the art would consider equivalent to the recited value (e.g., performing substantially the same function, acting in substantially the same way, and/or having substantially the same result). As used herein, the terms "about" or "approximately" in reference to a recited non-numeric parameter generally indicates that the recited non-numeric parameter encompasses a range of parameters that one of ordinary skill in the art would consider equivalent to the recited parameter (e.g., performing substantially the same function, acting in substantially the same way, and/or having substantially the same result).

Recitation of ranges of values herein are merely intended to serve as a shorthand method of referring individually to each separate value falling within the range, unless otherwise indicated herein, and each separate value is incorporated into the specification as if it were individually recited herein.

It should be noted that the terms "first", "second", and "third", and the like may be used herein to modify elements performing similar and/or analogous functions. These modifiers do not imply a spatial, sequential, or hierarchical order to the modified elements unless specifically stated.

In embodiments, a "patient" may be an animal in need of adjustment, correction, or supplementation of cardiac signaling or other function. The patient may be an animal where the animal may be a mammal, a reptile, or a bird. Still further, the animal may be a companion animal, an agricultural animal, a laboratory animal, a zoological animal, or a wild animal. The animal may be a human. The patient may be embryonic or fetal, infant, juvenile or pediatric, adolescent, young adult, adult, or geriatric. The age of the patient may range from pre-birth to 100 or more years old. The patient subject may be male, female, androgynous, or intersexual and of any ethnic origin.

"Biocompatible material(s)" as used herein may refer to materials that are safe to be implanted in a patient's body, including materials that are safe for temporary, but not permanent, implantation. "Biocompatible material(s)" as used herein may refer to materials that do not cause physical trauma or that cause minimal physical trauma; materials that are non-toxic or of low toxicity; materials that are not physiologically reactive or are minimally physiologically reactive; and/or materials that are not immunologically reactive or are minimally immunologically reactive. "Biocompatible material(s)" as used herein may refer to materials that have the ability to perform with an appropriate host response. "Biocompatible material(s)" as used herein may refer to materials that are or can be approved by the Food and Drug Administration ("FDA").

Certain embodiments may be implemented as a computer process, a computing system or as an article of manufacture such as a computer program product of computer readable media. The computer program product may be a computer storage medium readable by a computer system and encoding computer program instructions for executing a computer process.

The corresponding structures, material, acts, and equivalents of any means or steps plus function elements in the claims are intended to include any structure, material or act for performing the function in combination with other claimed elements. The description of certain embodiments has been presented for purposes of illustration and description, but is not intended to be exhaustive or limited to the form disclosed. Many modifications and variations will be apparent to those of ordinary skill without departing from the scope and spirit of the disclosure. These embodiments were chosen and described in order to best explain the principles of the disclosure and practical application, and to enable others of ordinary skill in the art to understand possible embodiments with various modifications as are suited to the particular use contemplated.

What is claimed is:

1. An implantable cardiac pace making system comprising:
   a first biocompatible implant comprising stimulator circuitry, an antenna, an exposed electrode, a photodiode, and a varactor; and
   a control module implant comprising a remote pulse generator,
   wherein the photodiode is configured to receive light from a light source and turn on the varactor, such that the varactor reflects a radio-frequency (RF) signal from the control module implant,
   wherein the varactor is configured to sense a biometric cardiac signal and modulate the sensed biometric cardiac signal onto a radio frequency-signal received from the control module implant,
   wherein the stimulator circuitry is configured to receive power via electromagnetic RF coupling from the control module implant,
   wherein the antenna is electrically connected to the stimulator circuitry and at least one of the photodiode and the varactor,
   wherein the control module implant is configured to receive backscattered electromagnetic (EM) waves from the first biocompatible implant both when the photodiode is active and when the photodiode is not active, and wherein the control module implant is configured to extract an ECG signal from the received backscattered EM waves;
   wherein the exposed electrode is electrically connected to the stimulator circuitry and at least one of the photodiode and the varactor; and
   wherein the implantable cardiac pace making system is fully-passive.

2. The system of claim 1, further comprising:
   a second biocompatible implant comprising stimulator circuitry, a second antenna, a second exposed electrode, a second photodiode, and a second varactor; and
   a third biocompatible implant comprising stimulator circuitry, a third antenna, a third exposed electrode, a third photodiode, and a third varactor.

3. The system of claim 2, wherein the first biocompatible implant, the second biocompatible implant, and the third biocompatible implant share the antenna and a time delay circuit, the antenna and time delay circuit being composed of inductors, capacitors, and diodes, and wherein the control module implant is configured to receive a multiplexed signal from the antenna and output a time-multiplexed multi-channel output signal.

4. The system of claim 1, wherein the control module implant is not physically connected to the first biocompatible implant.

5. The system of claim 1, wherein the sensor circuitry is further configured to sense a biometric cardiac signal and amplitude modulate the sensed biometric cardiac signal onto a radio frequency-signal received from the control module implant.

6. An implantable cardiac pace making system comprising:
   a first biocompatible implant comprising stimulator circuitry, a first exposed electrode, a first photodiode, and a first varactor;
   a second biocompatible implant comprising stimulator circuitry, a second exposed electrode, a second photodiode, and a second varactor;
   a third biocompatible implant comprising stimulator circuitry, a third exposed electrode, a third photodiode, and a third varactor; and
   a control module implant comprising a remote pulse generator,
   wherein the first photodiode is configured to receive light from a light source and turn on the first varactor, such that the first varactor reflects a first radio-frequency (RF) signal from the control module implant,
   wherein the second photodiode is configured to receive and reflect light from the light source and turn on the second varactor, such that the second varactor reflects a second radio-frequency (RF) signal from the control module implant,
   wherein the third photodiode is configured to receive and reflect light from the light source and turn on the third varactor, such that the third varactor reflects a third radio-frequency (RF) signal from the control module implant,
   wherein the first varactor, the second varactor, and the third varactor are each configured to sense a biometric cardiac signal and modulate the sensed biometric cardiac signal onto a radio frequency-signal received from the control module implant,
   wherein the first varactor, the second varactor, and the third varactor are each configured to receive power via electromagnetic RF coupling from the control module implant;
   wherein the control module implant is configured to receive backscattered electromagnetic (EM) waves both when each of the first photodiode, the second photodiode, and the third photodiode are active, and when each of the first photodiode, the second photodiode, and the third photodiode are not active, and wherein the control module implant is configured to extract an ECG signal from the received backscattered EM waves; and wherein the implantable cardiac pace making system is fully-passive.

7. The system of claim 6, wherein the first biocompatible implant, the second biocompatible implant, and the third biocompatible implant share an antenna and a time delay circuit, the antenna and time delay circuit being composed of inductors, capacitors, and diodes, and wherein the control module implant is configured to receive a multiplexed signal from the antenna and output a time-multiplexed multi-channel output signal.

8. The system of claim 6, wherein the control module implant is not physically connected to the first biocompatible implant.

9. The system of claim 6, wherein the sensor circuitry of the first biocompatible implant is further configured to sense a biometric cardiac signal and amplitude module the sensed biometric cardiac signal onto a radio frequency-signal received from the control module implant.

10. An implantable cardiac pace making system comprising:
- a first biocompatible implant comprising an antenna, an exposed electrode, a photodiode, and a varactor; and
- a control module implant comprising a remote pulse generator,
- wherein the photodiode is configured to receive light from a light source and turn on the varactor, such that the varactor reflects a radio-frequency (RF) signal from the control module implant,
- wherein the varactor is configured to sense a biometric cardiac signal and modulate the sensed biometric cardiac signal onto a radio frequency-signal received from the control module implant,
- wherein the antenna is electrically connected to at least one of the photodiode and the varactor,
- wherein the control module implant is configured to receive backscattered electromagnetic (EM) waves from the first biocompatible implant both when the photodiode is active and when the photodiode is not active, and wherein the control module implant is configured to extract an ECG signal from the received backscattered EM waves;
- wherein the exposed electrode is electrically connected to at least one of the photodiode and the varactor; and
- wherein the implantable cardiac pace making system is fully-passive.

11. The system of claim 10, wherein the first biocompatible implant further comprises stimulator circuitry and wherein the stimulator circuitry is configured to receive power via electromagnetic RF coupling from the control module implant.

12. The system of claim 10, further comprising:
- a second biocompatible implant comprising stimulator circuitry, a second antenna, a second exposed electrode, a second photodiode, and a second varactor; and
- a third biocompatible implant comprising stimulator circuitry, a third antenna, a third exposed electrode, a third photodiode, and a third varactor.

13. The system of claim 12, wherein the first biocompatible implant, the second biocompatible implant, and the third biocompatible implant share the antenna and a time delay circuit, the antenna and time delay circuit being composed of inductors, capacitors, and diodes, and wherein the control module implant is configured to receive a multiplexed signal from the antenna and output a time-multiplexed multi-channel output signal.

14. The system of claim 10, wherein the sensor circuitry is further configured to sense a biometric cardiac signal and amplitude modulate the sensed biometric cardiac signal onto a radio frequency-signal received from the control module implant.

15. The system of claim 10, wherein the first biocompatible implant comprises a flexible substrate.

\* \* \* \* \*